United States Patent
Yogesan et al.

(10) Patent No.: US 9,078,599 B2
(45) Date of Patent: Jul. 14, 2015

(54) IMAGER, MODULE FOR AN IMAGER, IMAGING SYSTEM AND METHOD

(75) Inventors: Kanagasingam Yogesan, Nedlands (AU); Carl Darius Blair, Nedlands (AU); Noam Allon, Nedlands (AU); Shari Eisenberg, Nedlands (AU)

(73) Assignee: Tagus Ventures, LLC, Fremont, CA (US)

( * ) Notice: Subject to any disclaimer, the term of this patent is extended or adjusted under 35 U.S.C. 154(b) by 544 days.

(21) Appl. No.: 13/435,160

(22) Filed: Mar. 30, 2012
(Under 37 CFR 1.47)

(65) Prior Publication Data
US 2013/0083184 A1    Apr. 4, 2013

Related U.S. Application Data

(63) Continuation-in-part of application No. PCT/AU2010/001282, filed on Sep. 30, 2010.

(30) Foreign Application Priority Data

Sep. 30, 2009 (AU) .............................. 2009904775

(51) Int. Cl.
| | |
|---|---|
| A61B 3/113 | (2006.01) |
| H04N 5/232 | (2006.01) |
| H04N 5/225 | (2006.01) |
| A61B 3/00 | (2006.01) |
| A61B 3/12 | (2006.01) |
| A61B 3/14 | (2006.01) |
| G02B 13/24 | (2006.01) |
| G02B 26/10 | (2006.01) |

(Continued)

(52) U.S. Cl.
CPC ............... *A61B 3/113* (2013.01); *A61B 3/0033* (2013.01); *A61B 3/1208* (2013.01); *A61B 3/14* (2013.01); *G02B 13/24* (2013.01); *G02B 19/009* (2013.01); *G02B 19/0028* (2013.01); *G02B 19/0066* (2013.01); *G02B 26/108* (2013.01); *G02B 27/143* (2013.01); *H04N 5/2251* (2013.01); *H04N 5/23212* (2013.01)

(58) Field of Classification Search
CPC ... A61B 3/113; H04N 5/2251; H04N 5/23212
USPC ..................................... 348/78; 351/206, 221
See application file for complete search history.

(56) References Cited

U.S. PATENT DOCUMENTS

| | | | | |
|---|---|---|---|---|
| 4,422,736 | A | 12/1983 | Nunokawa | |
| 5,508,760 | A * | 4/1996 | Kobayashi et al. | ........... 351/221 |
| 2004/0114057 | A1 * | 6/2004 | Yoon et al. | ..................... 348/744 |

(Continued)

FOREIGN PATENT DOCUMENTS

| | | |
|---|---|---|
| CN | 101536896 | 9/2009 |
| EP | 1 900 320 | 3/2008 |

(Continued)

*Primary Examiner* — Christopher S Kelley
*Assistant Examiner* — Matthew Kwan
(74) *Attorney, Agent, or Firm* — Martensen IP

(57) ABSTRACT

An imager (4) which may comprise a body (10) and an image sensor (20) housed within the body wherein the body may be releasably operably coupleable to a module (6), the module having an optical aperture (54) extending therethrough that aligns with the image sensor when operably coupled to the body to form an imaging channel wherein the sensor is operable to image a subject within an optical axis X of the imaging channel.

40 Claims, 15 Drawing Sheets

(51) Int. Cl.
*G02B 27/14* (2006.01)
*G02B 19/00* (2006.01)

(56) References Cited

U.S. PATENT DOCUMENTS

| | | |
|---|---|---|
| 2005/0171399 A1 | 8/2005 | Rich et al. |
| 2005/0200707 A1* | 9/2005 | Yogesan et al. .......... 348/207.99 |
| 2006/0146284 A1* | 7/2006 | Collins et al. ................. 351/221 |
| 2006/0147189 A1* | 7/2006 | Yogesan et al. ................. 396/18 |
| 2007/0195268 A1* | 8/2007 | Sarver et al. ................. 351/212 |
| 2008/0007693 A1* | 1/2008 | Williams et al. .............. 351/221 |
| 2008/0030679 A1* | 2/2008 | Yogesan et al. ............... 351/206 |
| 2008/0239070 A1* | 10/2008 | Westwick et al. ................ 348/68 |
| 2008/0319323 A1* | 12/2008 | Gravely et al. ............... 600/476 |
| 2009/0018419 A1* | 1/2009 | Torch ............................. 600/318 |
| 2009/0153797 A1* | 6/2009 | Allon et al. .................... 351/206 |

FOREIGN PATENT DOCUMENTS

| | | |
|---|---|---|
| JP | 2001356403 | 12/2001 |
| WO | WO 2006/118560 | 11/2006 |
| WO | WO 2008/040026 | 4/2008 |

\* cited by examiner

IMAGER, MODULE FOR AN IMAGER, IMAGING SYSTEM AND METHOD

RELATED APPLICATIONS AND INCORPORATION BY REFERENCE

This application is a continuation-in-part application of international patent application Serial No. PCT/AU2010/001282 filed 30 Sep. 2010, which published as PCT Publication No. WO 2011/038457 on 7 Apr. 2011, which claims benefit of Australian patent application Serial No. 2009904775 filed 30 Sep. 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to an imager, a module for an imager, and an imaging system and method and is particularly, although not exclusively, suitable for ocular imaging.

Throughout the specification, unless the context requires otherwise, the word "comprise" or variations such as "comprises" or "comprising", will be understood to imply the inclusion of a stated integer or group of integers but not the exclusion of any other integer or group of integers.

Furthermore, throughout the specification, unless the context requires otherwise, the word "include" or variations such as "includes" or "including", will be understood to imply the inclusion of a stated integer or group of integers but not the exclusion of any other integer or group of integers.

Additionally, throughout the specification, unless the context requires otherwise, the words "substantially" or "about" will be understood to not be limited to the value for the range qualified by the terms.

BACKGROUND ART

Each document, reference, patent application or patent cited in this text is expressly incorporated herein in their entirety by reference, which means that it should be read and considered by the reader as part of this text. That the document, reference, patent application, or patent cited in this text is not repeated in this text is merely for reasons of conciseness.

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

Apparatus, systems and methods have been disclosed for ocular imaging. However, these typically have one or more problems.

In the case of retinal imaging:
corneal reflection and scattering from the internal eye lens may be present in the imaging path, reducing the clarity of images that can be taken;
they inhomogeneously illuminate structures of the eye to be imaged, such as the retina;
they do not provide enhanced fluorescein angiography, autofluorescence and indocyanine green angiography imaging;
internal reflections and/or surface specula reflections from outside the imaging system may be present in the imaging path, producing artefacts in the images taken; and
they do not allow for small pupil illumination or small pupil imaging to be performed, resulting in reduced image quality.

In the case of slit lamp imaging, the Light Emitting Diode ("LED") based light sources used typically suffer from a lack of brightness. Such imaging apparatus and systems also typically have poor slit quality and a simplistic construction. In the case of reflex imaging they require the pupil of the eye to be dilated—restricting them to mydriatic reflex imaging for procedures such as imaging the ocular lens for cataract diagnosis and grading.

In the case of non-invasive imaging of the tear film, prior art approaches of using a conical light guide require sophisticated optical engineering to achieve suitable uniform illumination and adequate brightness for satisfactory imaging.

In International Patent Application, Publication No WO 2006/016366 A2 a large and complex retinal imager is described which is not suitable for hand held use or portability. The retinal imager does not support a comprehensive set of imaging techniques to address common eye disease, especially those apparent in the anterior segment of the eye. The retinal imager also does not significantly address problems with coincidence of infrared and white light illumination, resulting in reduced image quality in an infrared preview mode.

International Patent Application, Publication No WO 2005/122874 A1 describes an ophthalmic camera and an ophthalmic camera adaptor which also do not significantly address problems with some of the reflections and coincidence of infrared and white light illumination.

The ophthalmic camera described in International Patent Application, Publication No WO2004/112599 A1 also does not significantly address problems with coincidence of infrared and white light illumination. It also does not support a comprehensive set of imaging techniques to address common eye disease, especially those apparent in the anterior segment of the eye.

The portable slit lamp disclosed in International Patent Application, Publication No WO01/89375 A1 does not support a comprehensive set of imaging techniques to address common eye disease, especially those apparent on the retina of the eye.

Citation or identification of any document in this application is not an admission that such document is available as prior art to the present invention.

SUMMARY OF THE INVENTION

The present invention seeks to provide an imager, system and method that alleviates some or all of the above mentioned problems associated with the prior art to at least some extent, or to provide the consumer with a useful or commercial choice.

Other advantages of the present invention will become apparent from the following description, taken in connection with the accompanying drawings, wherein, by way of illustration and example only, preferred embodiments of the present invention are disclosed.

In accordance with a first broad aspect of the present invention, there is provided an imager which may comprise:

a body; and an image sensor supported by the body wherein the body is releasably operably coupleable to a module, the module having an optical aperture extending therethrough that aligns with the image sensor when operably coupled to the body to form an imaging channel wherein the sensor is operable to image a subject within an optical axis of the imaging channel.

The image sensor may be housed within the body.

Preferably, the imager further may comprise a camera lens for focussing the subject image on the image sensor. The camera lens may be housed within the body of the imager or the module.

Preferably, the module may comprise projection means for emitting radiation along the imaging channel for radiating the subject for a diagnostic purpose. Preferably, the projection means may comprise optics. Preferably, the projection means may comprise radiation emitting means. The radiation emitting means may comprise one or more Light Emitting Diodes ("LED").

Preferably, when the subject is an eye, the camera lens may comprise an entrance pupil, wherein the entrance pupil is such that there is substantially no overlap between a conjugate of the entrance pupil and a conjugate of an image of the projection means in a corneal plane.

Preferably, the imager may comprise a selector operable to enable the wavelength of the radiation emitted by the radiation emitting means to be selected according to the diagnostic purpose. Preferably, when the diagnostic purpose is colour retina imaging, the wavelength selection corresponds to white light; when the diagnostic purpose is fluorescein angiography imaging, the wavelength selection corresponds to cyan light; when the diagnostic purpose is ndocyanine green angiography, the wavelength selection corresponds to infrared light; when the diagnostic purpose is autofluorescence imaging, the wavelength selection corresponds to cyan or amber light; when the diagnostic purpose is retina imaging, the wavelength selection corresponds to white or infrared light; when the diagnostic purpose is slit lamp imaging, the wavelength selection corresponds to white or infrared light; when the diagnostic purpose is tear film imaging, the wavelength selection corresponds to white light; and when the diagnostic purpose is topical fluorescein imaging, the wavelength selection corresponds to cyan light. To detect a specific diagnostic feature any wavelength or combination of wavelengths that best or most advantageously highlights or displays the specific feature may be chosen, such as using wavelengths corresponding to red light or infrared for choroid features and wavelengths corresponding to green light for vascular features, for example.

Preferably, the imager further may comprise positioning means for moveably positioning the image sensor relative to and/or within the body.

Preferably, the imager further may comprise control means operable to control the sensor and/or the module.

In accordance with a second broad aspect of the present invention, there is provided a module for an imager having a body and an image sensor supported by the body, the module which may comprise:

means for releasably operably coupling to the body; and and optical aperture extending therethrough wherein, when operably coupled to the body, the optical aperture aligns with the image sensor to form an imaging channel wherein the sensor is operable to image a subject within an optical axis of the imaging channel.

Preferably, the module further may comprise a camera lens for focussing the subject image on the image sensor.

Preferably, the module may comprise projection means for emitting radiation along the imaging channel for radiating the subject for a diagnostic purpose. Preferably, the projection means may comprise optics. Preferably, the projection means may comprise radiation emitting means. The radiation emitting means may comprise one or more Light Emitting Diodes ("LED").

Preferably, the imager may comprise a selector operable to enable the wavelength of the radiation emitted by the radiation emitting means to be selected according to the diagnostic purpose. Preferably, when the diagnostic purpose is colour retina imaging, the wavelength selection corresponds to white light; when the diagnostic purpose is fluorescein angiography imaging, the wavelength selection corresponds to cyan light; when the diagnostic purpose is indocyanine green angiography, the wavelength selection corresponds to infrared light; when the diagnostic purpose is autofluorescence imaging, the wavelength selection corresponds to cyan or amber light; when the diagnostic purpose is retina imaging, the wavelength selection corresponds to white or infrared light; when the diagnostic purpose is slit lamp imaging, the wavelength selection corresponds to white or infrared light; when the diagnostic purpose is tear film imaging, the wavelength corresponds to white light; and when the diagnostic purpose is topical fluorescein imaging, the wavelength corresponds to cyan light. To detect a specific diagnostic feature any wavelength or combination of wavelengths that best or most advantageously highlights or displays the specific feature may be chosen.

Preferably, when the subject is an eye having a retina, the projection means is operable to image the retina. Preferably, the projection means may comprise a first radiation emitting means emitting radiation in a first wavelength, and a second radiation emitting means emitting radiation in a second wavelength. Preferably, the first radiation emitting means may comprise a first set of LEDs emitting white light radiation, and the second radiation emitting means may comprise a second set of LEDs emitting infrared radiation. Preferably, the first set of LEDs and the second set of LEDs are positioned radially with respect to the optical axis of the imaging channel and aligned to generate a beam of radiation that is substantially uniform at an intermediate image plane. Preferably, individual LEDs of the second set of LEDs are positioned symmetrically about the optical axis of the imaging channel.

Preferably, when the subject is an eye, the camera lens has an entrance pupil, wherein the entrance pupil is such that there is substantially no overlap between a conjugate of the entrance pupil and a conjugate of an image of the projection means in a corneal plane.

Preferably, the module may comprise reflection removing means for removing reflections from the imaging channel. Preferably, the reflection removing means may comprise at least one component selected from the group which may comprise a polariser, an analyser, a stop and/or an aperture.

Preferably, the module may comprise chromatic aberration removing means for removing chromatic aberration from the illumination and imaging channel. Preferably, the chromatic aberration removing means may comprise a shell shaped lens.

Preferably, the module may comprise optical shifting means operable to shift an apparent position of the projecting means relative to the optical axis of the imaging channel.

Preferably, the optical shifting means may comprise at least one lens selected from the group which may comprise a prismatic lens, a wedge lens, and a negative lens.

Preferably, the projection means is arranged or operable to facilitate fluorescein angiography, indocyanine green angiography and autofluorescence imaging of the subject.

Preferably, the projection means is arranged or operable to function as a slit lamp. Preferably, the projection means may comprise background radiation emitting means for illuminating the subject. Preferably, the background radiation emitting means may comprise an LED emitting white light radiation. The projection means may comprise a slit generation module. The slit generation module may comprise radiation emitting means optically aligned with a mask having a predetermined pattern, wherein the mask is operable to allow emitted radiation to pass therethrough in the predetermined pattern.

Preferably, the module may comprise radiation removing means for removing radiation of a predetermined wavelength from the imaging channel. Preferably, the predetermined wavelength is infrared, in which case the radiation removing means may comprise an infrared filter.

Preferably, when the subject is an eye having a pupil, the projection means is arranged or operable to image red and infrared reflex of the eye. In this case, the projection means may comprise a beam splitter received within the aperture, a first radiation emitting means emitting radiation in a first wavelength positioned normal to the plane of the aperture, a second radiation emitting means emitting radiation in a second wavelength positioned parallel to the plane of the aperture, and a dichroic filter positioned between the first radiation means and the second radiation means, the dichroic filer and beam-splitter being operable to couple radiation emitted in the first wavelength to radiation emitted in the second wavelength and direct the coupled radiation along the imaging channel into the pupil of the eye.

Preferably, when the subject is an eye having a tear film, the projection means is arranged or operable to image the tear film. Preferably, the projection means may comprise a light guide containing the optical aperture, and radiation emitting means disposed along at least a portion of the light guide. Preferably, the radiation emitting means may comprise a multitude of LEDs equispaced and equidistant radially about the light guide attached to the inner surface of a reflective peripheral wall of the light guide.

Preferably, the projection means is arranged or operable to facilitate topical fluorescein imaging of the subject.

In accordance with a third broad aspect of the present invention, there is provided an imaging system which may comprise:

an imager in accordance with the first aspect of the present invention as hereinbefore described;
a module for an imager in accordance with the second aspect of the present invention as hereinbefore described operably coupled to the imager; and
a processor
wherein images captured by the imager are communicated to the processor for storage and/or further processing.

In accordance with a fourth broad aspect of the present invention, there is provided an imaging method which may comprise:

aligning an optical aperture in a module with an image sensor to form an imaging channel; and
imaging a subject within an optical axis of the imaging channel via the image sensor.

In accordance with a fifth broad aspect of the present invention, there is provided a computer-readable storage medium on which is stored instructions that, when executed by a computing means, causes the computing means to perform the imaging method according to the fourth broad aspect of the present invention as hereinbefore described.

In accordance with a sixth broad aspect of the present invention, there is provided a computing means programmed to carry out the imaging method according to the fourth broad aspect of the present invention as hereinbefore described.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

In order that the invention may be more fully understood and put into practice, a preferred embodiment thereof will now be described, by way of example only, with reference to the accompanying drawings, in which.

DETAILED DESCRIPTION OF THE INVENTION

Figure 1:
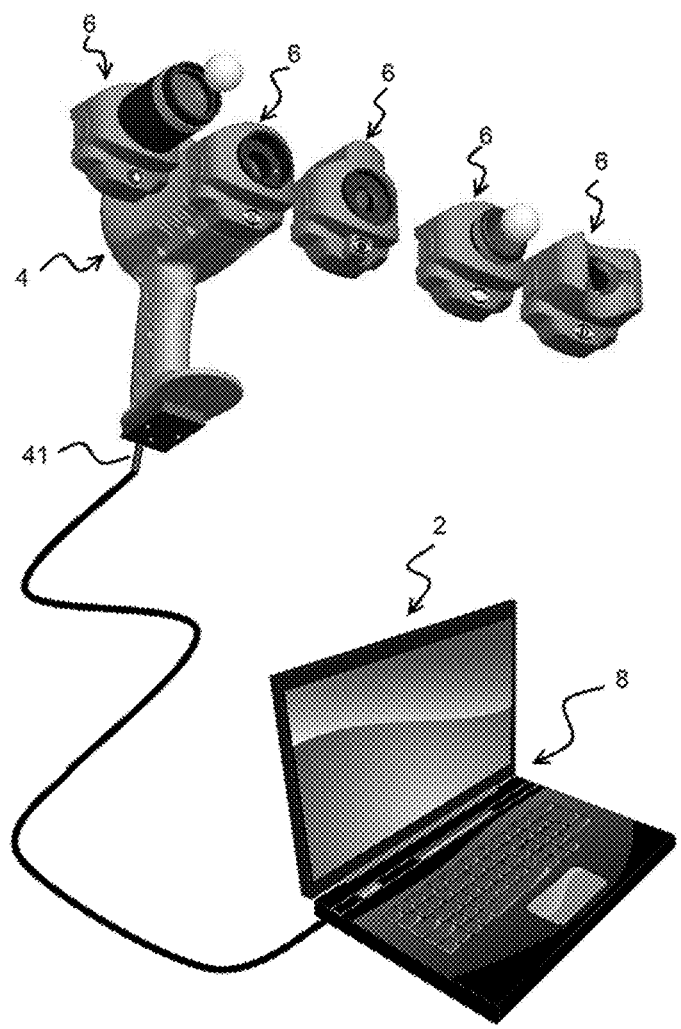
FIG. 1 depicts a schematic representation of components that form an embodiment of an imaging system in accordance with an aspect of the present invention.

In FIG. 1, there shown a first embodiment of an imaging system 2 in accordance with an aspect of the present invention.

In the embodiment described, the imaging system 2 is used for ocular examination in a clinical or screening setting.

The imager, system and method of the present invention is not limited to such examination, however, and alternative embodiments may be used in the examination of subjects or anatomy other then eyes, including, for example aural examination, or dental examination.

The imaging system 2 comprises an imaging device or apparatus in the form of an imager 4, a plurality of imaging adapters or modules 6 releasably operably coupleable to the imager 4, and an imaging software application ("application") stored and run on a computer 8 in data communication with the imager 4.

The imager 4 and the application perform imaging and control functions in relation to the ocular examination whilst the modules 6 provide optics and illumination for particular ocular examination procedures.

Figure 2:
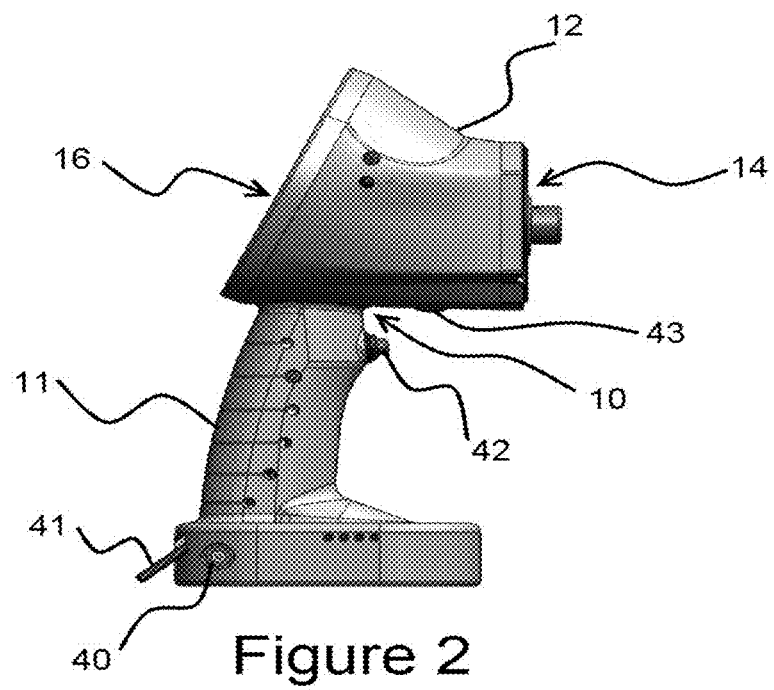
FIG. 2 depicts a right side view of the imager of the imaging system of FIG. 1.
Figure 3:
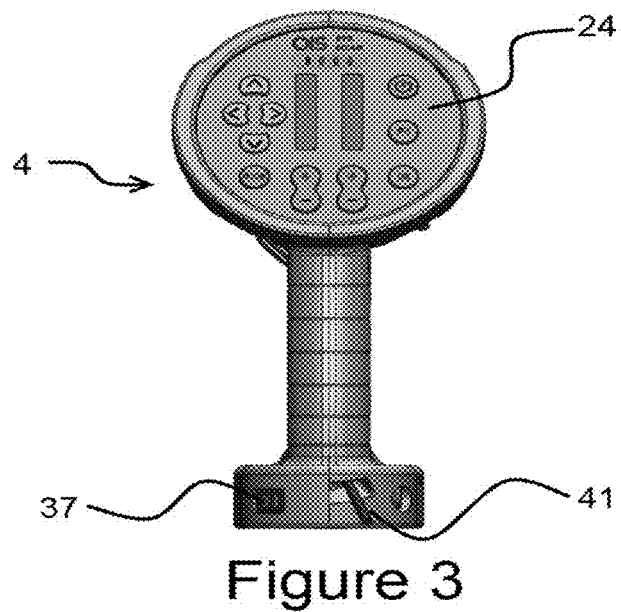
FIG. 3 depicts a rear or back view of the imager of FIG. 2.
Figure 4:
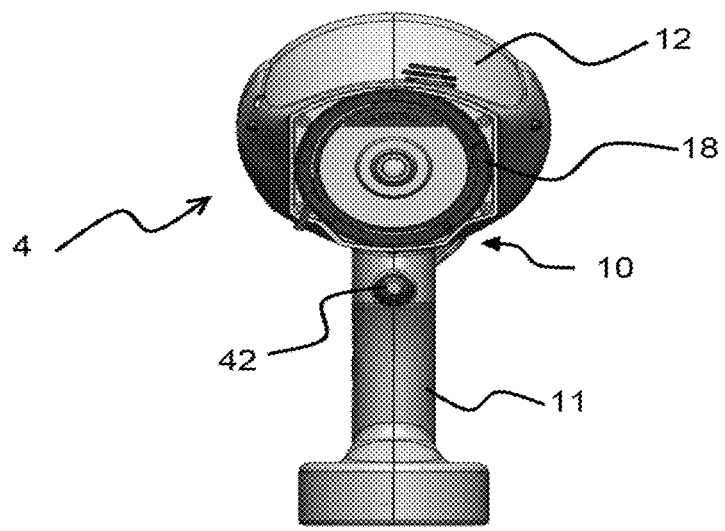
FIG. 4 depicts a front view of the imager of FIG. 2.
Figure 5:
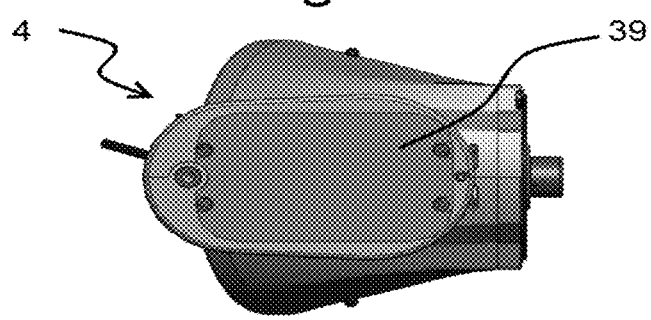
FIG. 5 depicts a bottom view of the imager of FIG. 2.
Figure 6:
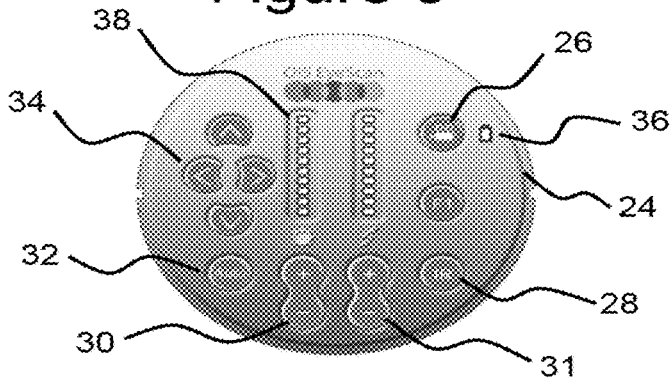
FIG. 6 depicts a view of a control panel of the imager of FIG. 2.

As illustrated in FIG. 2 of the drawings, the imager 4 comprises a casing or body 10 having a handle 11 extending from a head portion 12 having a first or front end 14 and a second or back/rear end 16 opposed thereto. The front end 14 of the body 10 is configured to receive and securely retain a module 6 by means of a bayonet mounting 18. In alternative embodiments of the invention, other means may be provided for releasably coupling a module 6 to the imager 4, such as snap clips, for example.

Figure 14:
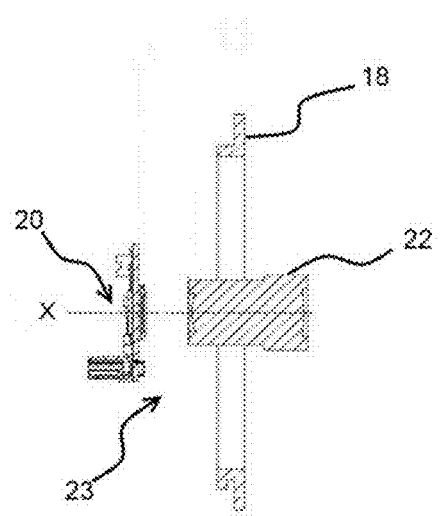
FIG. 14 depicts a schematic diagram of optical and other components of the imager of FIG. 1.

The head portion 12 in one configuration supports and houses optical components of the imager 4 as illustrated in FIG. 14 of the drawings. In the embodiment described, the optical components of the imager 4 comprise an image or optical sensor 20 aligned with a camera lens 22 projecting or protruding substantially centrally from the front end 14 of the imager 4. Together, the optical sensor 20 and the camera lens 22 form an imager camera 23. In another configuration, the camera lens 22 is provided on the module 6, leaving only the optical sensor 20 in the head portion 12.

The optical sensor 20 and the camera lens 22 are aligned along an optical axis X. The optical sensor 20 is mounted on a positioner or positioning means in the form of a slidable assembly or carriage (not shown) within the body 10 including a stepper motor such that the position of the optical sensor 20 is selectably moveable along the optical axis X. This is advantageous as it allows for the position of the optical sensor 20 relative to the camera lens 22 to be dynamic rather than fixed, thereby providing a range of focus. Furthermore, it provides a simplified unified focus mechanism for all modules 6 with correct camera lens 22 design. Selection of the position of the optical sensor 20, and operation of other functions of the imaging system 2, is provided by means of user interface or control means (or a controller/selector) which are described in further detail below.

In the embodiment described, the optical sensor 20 is a 5 megapixel resolution complementary metal-oxide-semiconductor ("CMOS") sensor sensitive to visible light (with colour representation) and infrared light, and operable to capture images and videos in several resolutions and frame rates. In alternative embodiments of the invention, alternative imaging sensors or cameras may be used, such as a charge coupled device ("CCD") sensor, and of any resolution, provided that they are able to produce images of suitable quality.

In the embodiment described, the user interface/control means comprises the software application and components of the computer 8, described in further detail below, and user controls provided on a control panel 24 on the rear end 16 of the imager 4. This control panel in an alternate configuration is composed of a touch screen with live preview in addition to the features described below. The user controls are operably connected to the components of the imaging system 2 to allow the user to adjust or otherwise control the optics and/or operation of the imager 4 and modules 6 when coupled thereto. This will be described in more detail below.

User controls provided on the control panel 24 include:

- a video enable/disable button 26, operable to enable the imaging system 2 to toggle between a first mode that captures or records videos and a mode that captures or records still images via the optical sensor 20;
- an infrared/visible light button 28, operable to enable selection of a desired mode of operation for modules 6 having infrared and visible light modes of operation. This button 28 toggles between an infrared preview mode (in which it is illuminated) and a visible light preview mode (in which it is dim);
- flash brightness or intensity control buttons 31, operable to selectively increase (brighten the exposure) and decrease (darken the exposure) of a flash brightness of a module 6 during an image capture process. The flash is generated by LEDs of the module 6 of whichever colour is required for the final image to be captured. As will be described in further detail below, for colour retina imaging modules these are white light emitting LEDs, for fluorescein angiography imaging modules—cyan (~480 nm) light emitting LEDs, for autofluorescence imaging modules—cyan (~480 nm) or amber (~560 nm) light emitting LEDs, for retina imaging modules—white or infrared (~770 nm-900 nm) light emitting LEDs depending on the mode of operation, for slit lamp module imaging—white slit LEDs, for tear film imaging modules—white light emitting LEDs, and for topical fluorescein imaging modules—cyan (~460 mn) light emitting LEDs. In embodiments of the invention, to detect a specific diagnostic feature any wavelength or combination of wavelengths that best or most advantageously highlights or displays the specific feature may be chosen;
- preview brightness or intensity control buttons 30, operable to selectively increase and decrease a brightness of an image;
- automatic illumination enable/disable button 32, operable to enable the software application to automatically select preview and flash brightness and/or illumination levels during an image capture process To achieve this, the software application is operable to conduct an image analysis of the preview image to determine whether a certain prescribed preview brightness is achieved, then to reference a look up table to translate to an appropriate flash brightness. This button 32 toggles between such an automatic mode (in which it is illuminated) and a manual mode (in which it is dim) for manual control of these parameters by a user;
- up/down/right/left selection buttons 34, operable to control which of a patients eyes is to be imaged (left/right buttons) (in the case that the laterality is recorded automatically these are operable to indicate the eye being imaged), to provide an indication of whether a module 6 is correctly coupled to the imager 4 (up button blinking) and when the system 2 has switched to a standby mode (down button blinking);
- a battery status indicator 36; and
- selection level indicators 38. These are operable to provide an indication of the preview brightness incident on the eye and the flash "brightness" or energy that the eye will receive during the exposure of the optical sensor 20. Having such an indication allows a user to assess whether the levels will be sufficient for the required imaging procedure, whilst not being detrimental to the vision of the patent, before proceeding further.

Power supply to the imager 4 is provided by means of batteries housed in a compartment 39, via a universal serial bus ("USB") connection 41 to the computer 8, and by an optional DC source (not shown) connected by an external power jack 40 by appropriate circuitry to provide power to the imager 4, the components thereof, and a module 6 coupled thereto. The imager 4 has an on/off switch 37. The provision of power to electronic devices is well known to persons skilled in the art and, as such, need not be described in any further detail herein, except as is relevant to the present invention.

The user controls further comprise a trigger button 42 provided on the handle 11. In alternative embodiments of the invention, a trigger button can also be implemented as an operably connected foot or pedal control button or on a chin-rest assembly 105. A focusing wheel 43 is also provided on the head portion 12. Both of these are positioned such that they can be conveniently manipulated by a user holding the handle 11.

The trigger button 42 is used in handheld operation for automatic image focusing and image capture. A half depression of the trigger button 42 initiates an automatic focus process or routine. Once the automatic focus routine is executed, the application is operable to generate an alert indicating that it is ready to capture an image. Subsequent full depression of the trigger button 42 operates the application to capture the image that the optical sensor 20 is focused on and store it in a memory of the computer 8.

Use of the focus wheel 43 provides a linear focus shift for each module 6. Such use overrides the automatic focus feature and facilitates manual focusing (by movement of the carriage on which the optical sensor 20 is mounted) by a user. When using retinal imaging modules 6, the focus adjustment is linear in Diopters. In other modules 6, the focus shift is linear with focus distance. The manual focus adjustment is proportional to the speed that the manual focus wheel is rotated in a weighted function to provide a natural "feel" to the user.

As described above, the imager 4 is connected to the computer 8 via a USB connection. In alternative embodiments of the invention, other wired or wireless means with appropriate protocols may be used to facilitate communication between the components of the imaging system 2.

In the embodiment described, the application stored and run on the computer 8 comprises software provided under the trade mark WinStation by Ophthalmic Imaging Systems. The application can be written in any suitable language, and can be provided as a standalone application or via network depending on the system requirements.

The computer 8 can be of any suitable type, such as a personal laptop computer.

The computer 8 includes display means in the form of a monitor or visual display, control means such as a keyboard and other suitable peripheral devices such as a mouse to enable a user to interact with the application. The computer 8 also includes processing means such as a central processor and storage means such as a memory device for the storage and running of an operating system such as Windows®, and one or more software applications, including the application of the embodiment of the present invention. The use and operation of computers using software applications are well known to persons skilled in the art and need not be described in any further detail herein except as is relevant to the present invention.

In an alternative embodiment of the invention, rather than requiring connection to the computer 8, the optical sensor 20 is operably connected by appropriate circuitry to capture and record images in a storage means housed in the body 10 of the imager 4. The storage means may comprise a memory device and may be releasably connectable to the circuitry by interface means such as a memory slot. Any appropriate storage technology may be used, including a USB storage option or a small memory card, such as a flash memory card, for example. In alternative embodiments of the invention, the computer 8, and/or components thereof or equivalent components such as a display means such as a viewing screen, may be provided in the body 10 of the imager 4, and preferably on the control panel 24 on the rear end 16 of the imager 4, and operably connected by appropriate circuitry. This may make performing operations using the imager 4, such as image focusing and preview, easier during handheld use.

Data received by the computer 8 (inputted by the user via the control means or from the imager 4) is stored in a database coupled to the computer 8 and in data communication therewith in order to enable data to be read to and from the database, as is well known to persons skilled in the art. Any suitable database structure can be used. The database can be provided locally as a component of the computer 8 (such as in the storage means) or remotely such as on a remote server. In this embodiment, several computers can be set up this way to have a network client-server application. There is one database of information for the application in the embodiment described and it is stored in the storage means of the computer 8. In alternative embodiments there may be more than one database of information.

The software application is operable to perform a number of functions, including:
  image acquisition;
  record/store and review and process acquired images in a patient record in the database, the patient record comprising information related to the patient being examined and having their eye imaged;
  control many of the operational settings of the imager 4, loading them upon execution or runtime into firmware of the imager 4; and
  image processing control during or after image acquisition, such as brightness, contrast, gamma, colour balance and many more advanced options such as montage, and disease grading, for example.

Each module 6 is designed to provide a different diagnostic function, allowing the imaging system 2 to be multi-purpose. The modules 6 have a generic construction as shown in the drawings and this will now be described. The optical, electronic and other custom components of each module 6 will be described separately.

As shown in the drawings, each module 6 comprises a module body 44. Each module body 44 houses the optics, electronics and other components of the module 6, and is shaped accordingly. In each case in the embodiment described, the module body 44 has a first or front end 46 and a second or rear end 48.

The rear end 48 is provided with a bayonet mounting 50 complimentary to the bayonet mounting 18 of the imager 4 to allow the module 6 to be releasably coupled thereto. Provided adjacent the bayonet mounting 50 is an interface contact (not shown) for operably engaging or coupling the module 6 to the imager 4 so that the functions of the module 6 may be controlled by the user interface/control means.

Located centrally about a rear face 52 of the rear end 48 is an optical aperture 54. The aperture 54 extends through the module 6 such that the aperture 54 is also located centrally about a front face 56 of the front end 46. Optical components of the module 6 are aligned along an optical axis Y of the aperture 54.

When a module 6 is operably coupled to the imager 4:
  the optical aperture 54 aligns with the camera lens 22 of the imager 4. In this position, the optical axis Y of the module 6 aligns with the optical axis X of the imager 4 to provide an unimpeded optical axis of an imaging channel or path such that at least a portion of the optical axis X is not obscured by the remainder of the module 6; and
  module 6 is operably interfaced with the imager 4.

The optical, electronic and other custom components of each module 6 will now be described.

Figure 7:
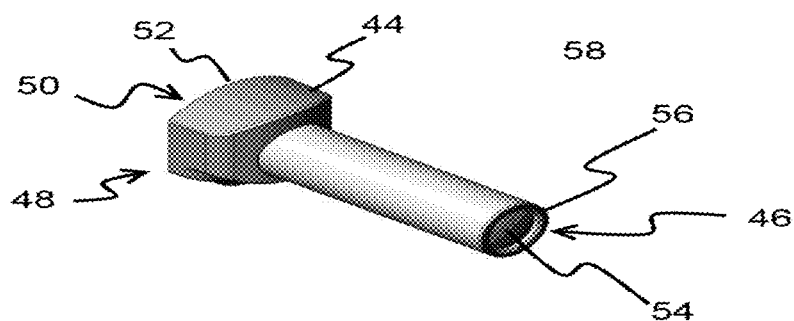
FIG. 7 depicts a front perspective view of a mydriatic or non-mydriatic retina module of the imaging system of FIG. 1.

A mydriatic retina module 58 is illustrated in FIG. 7. A non-mydriatic retina module has a similar appearance. The retina module 58 is for imaging the fundus or retina of an eye, and has two modes of operation: infra red preview mode, where image preview and capture is performed in a dark room with infrared light, and white light preview mode where image preview and capture is typically performed with white light on a dilated eye.

Figure 15A:
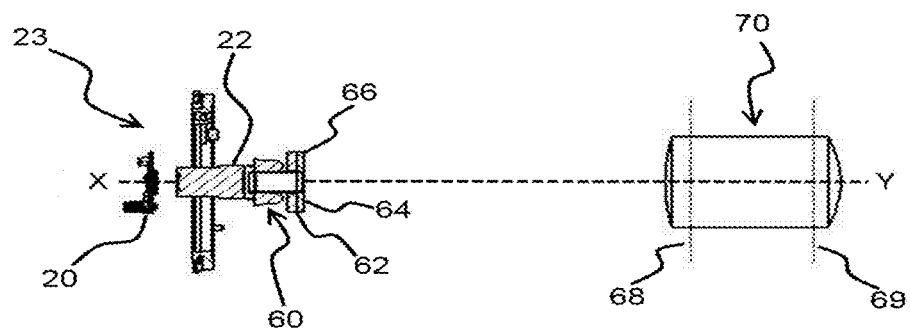
FIG. 15A depicts a schematic diagram of optical and other components of the mydriatic retina module of FIG. 7 in a large pupil mode of operation.
Figure 15B:
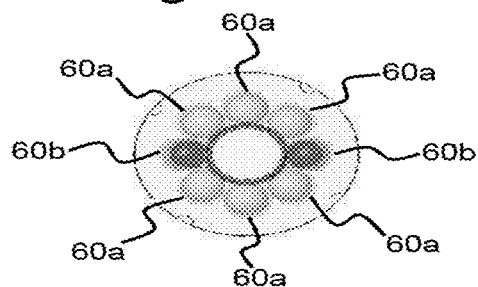
FIG. 15B depicts a front view of placement of LEDs of the mydriatic retina module of FIG. 7 in a normal pupil mode of operation.
Figure 15C:
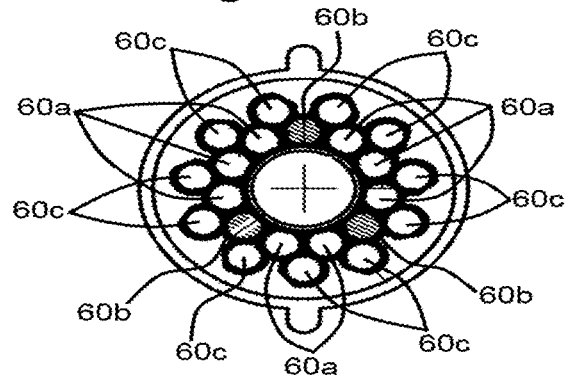
FIG. 15C depicts a front view of placement of LEDs in an alternative configuration of the mydriatic retina module of FIG. 7 which facilitates small pupil and large pupil modes of operation in a single module.

In another embodiment shown in FIG. 15C the mydriatic retina module has two more modes of operation, a small pupil mode of operation where only white LEDs 60*a* (a subset of the LEDs) are used for imaging (and preview in white light preview mode) and a normal pupil mode of operation, where white LEDs 60*a* and 60*c* are using for imaging (and preview in white light preview mode). While infra red LEDs 60*b* are used for preview in small pupil and normal pupil mode when using infra red preview mode of operation. In the embodiment described, three LEDs 60*b* are provided and are arranged in a triangular formation around the optical axis Y. This configuration advantageously provides for homogeneous illumination. Preferably, the LEDs 60*b* are positioned in the most rotationally symmetrical way possible. In this way the preview image is uniformly illuminated when aligned correctly.

Optical components of the mydriatic retinal module 58 are illustrated in FIG. 15A.

In the mydriatic retina module 58, a projector or projection means comprising radiation emitting means is provided in the form of a plurality of Light Emitting Diodes ("LEDs") 60 positioned in a recess in the mydriatic retina module 58 adjacent to the rear face 52 thereof and parallel to the optical axis Y so as to emit radiation in a direction along the optical axis Y of the aperture 54 and towards the optical components provided therein. The recess holds the LEDs 60 pointed a few degrees into the optical axis Y and acts as a baffle to prevent stray light. The LEDs 60 are aligned in such a way that the beam of radiation emitted thereby is uniform at an intermediate image plane behind an ophthalmic or retinal lens system 70.

In the embodiment described, the LEDs 60 are symmetrically distributed in a ring formation radially around the optical axis Y, and comprise a first set of six LEDs 60*a* operable to emit radiation having a first wavelength—white light radiation, and a second set of two LEDs 60*b* operable to emit radiation having a second wavelength—infrared radiation. The placement of the LEDs 60, as illustrated in FIG. 15B of the drawings, are such that the infrared emitting LEDs 60*b* are placed at positions of 90 degrees and 270 degrees circumferentially around the optical axis Y, whilst the white light emitting LEDs 60*a* are placed at positions of 0 degrees, 45 degrees, 135 degrees, 180 degrees, 225 degrees, and 315 degrees circumferentially around the optical axis Y. This orientation with the infrared emitting LEDs 60*b* at either side is advantageous because they are less likely to be obscured by the eyelids of the patient during an alignment process prior to image capture. If they are obscured, for example in the case of a patient having droopy eyelids, the eyelids must only be held open during the flash/exposure of the image capturing process.

In alternative embodiments of the invention, other combinations or sequencing of infrared and white light emitting LEDs can be used, such as, 4 white light+4 infrared, 5 white light+3 infrared, or 19 white light+3 infrared, for example, as in the alternative configuration illustrated in FIG. 15C advantageously providing for both small pupil illumination and large pupil illumination in one module. Embodiments of the invention can have any number of LEDs, including more than eight or less than eight. Indeed, any number or combination of radiation emitting means emitting radiation having any wavelength positioned in any sequence can be used in alternative embodiments of the invention and in modules 6, depending on the application and the imaging to be performed.

In embodiments of the invention, a range of very specific wavelengths can be selected for illumination of the retina or other structures of the eye according to the imaging to be conducted. Configurations include white light sources (for white light preview mode retina imaging), white and infrared sources (for infra red preview mode retina imaging), cyan sources (for fluorescein angiography), amber or cyan sources (for autofluorescence), and infrared sources (for indocyanine green angiography), as will be described in further detail below. Different wavelengths image different layers of the retina. For example red or infrared wavelengths image the deeper layers of the retina (choroids) while green wavelengths provide most contrast for vascular and blues the nerve fibre layers.

In the white light preview mode of operation, the white light emitting LEDs 60a are used in the preview process, being activated via the infrared/visible light button 28.

When the mydriatic retina module 58 is coupled to the imager 4, the positioning of the LEDs 60 is such that they are distributed about or around a periphery of the camera lens 22 of the imager 4. The camera lens 22 is designed with a specific entrance pupil such that there can be substantially no, or reduced, overlap between the conjugate of the entrance pupil of the imager camera 23 and the conjugate of the LED image in the corneal plane. In this way, light enters the eye such that corneal reflection and scattering from the internal eye lens are removed from the imaging path.

This structure provides a means of placing a radiation or light source (the LEDs 60) in the conjugate plane of the pupil in the retina module 58. This is advantageous as the conjugate (or image of, which is roughly in the corneal plane) of the LEDs 60 and the entrance pupil of the imager camera 23 are well separated in all possible working positions and through all possible scattering and reflective surfaces. In this way these scattering and reflective surfaces will not affect image quality.

Provided along the optical axis Y, between the LEDs 60 and the front face 56 of the front end 46 of the retina module 58, are optical components including radiation removing means or remover in the form of an infrared cut filter 62, reflection removing means or remover in the form of an illumination polariser 64 and an analyser 66, being a polariser set at 90 degrees to the illumination polariser 64, chromatic aberration correcting or compensating means or corrector in the form of a shell or correction lens 68, and an objective lens 69. The above referenced retinal lens system 70 comprises the shell lens 68 and the objective lens 69.

The infrared cut filter 62 takes out unwanted infrared light from the ambient light and from the white light emitting LEDs 60a. Removing any stray/ambient light is advantageous. In the embodiment described, the optical sensor 20 of the imager camera 23 is sensitive to infrared light by design (so one sensor can be used for both image preview and flash. Infrared light, however, interferes with natural colour representation as it is not a "colour" that the human eye can interpret and is represented in the image as a pinky grey colour. Removing this light from the illumination channel gives back or restores natural colour representation to the images. In alternative embodiments of the invention, where the imager sensor is not sensitive to infrared light, an infrared filter is not required.

Internal reflections in the optical system of the retina module 58 that are not removed or mitigated by anti-reflective ("AR") coatings on the shell lens 68 and the objective lens 69 are removed by polariser 64 and analyser 66 and also attenuate any surface specula reflections from outside the retina module 58.

In an alternative embodiment of the invention, a spot stop is used to remove the light from the illumination beam that would be responsible for internal reflections and, to a large degree, specular reflections of the cornea. This is achieved by making a slightly more complex illumination projection system, an example of which is illustrated in FIG. 16C of the drawings, where an image of one or several spot stops is created on the surfaces of the shell lens 68, the objective lens 69 and the cornea. The benefit is that polarisers "waste" a lot of light. If a spot stop is used to avoid these reflections before they happen then all the light incident on the eye can be used for the image.

In this configuration, LEDs 71, with associated light projection assemblies (LPAs) which may contain appropriate optical components such as masks, collimate light or lens L1 is used to collimate light, and spot stops are imaged by lens L2 onto the ophthalmic systems surfaces. A ring of incoupling mirrors M is projected onto the cornea of the eye leaving a clear imaging aperture in center of pupil. A uniform beam at an intermediate image (behind the ophthalmic lens system) is projected by the ophthalmic lens and eye lens onto the retina.

Chromatic aberration in the imaging channel results in reduced image clarity and a specific distortion in shapes and colours. The shell shaped lens 68 eliminates chromatic aberration between infrared (for non-mydriatic imaging) and visible light—thereby correcting for chromatic aberration in the illumination path or imaging channel such that infrared and visible illumination is coincident. In this manner, the infrared image is more representative of the white light image and there is less reliance on alignment aids.

In the prior art, the illumination is made coincident on the cornea of the eye such that an adequate infrared image can be seen for eye positioning but not for confirmation of alignment or a presentation of image quality. Often alignment aids are not useful, such as when viewing the periphery of the eye or when anterior shots of the eye are taken, in these cases a true infrared representation is preferred and is achieved by the above described solution.

Function of the shell lens 68 will now be described in further detail with reference to FIG. 16D of the drawings. A main design constraint of any retina imaging camera is to obtain a large working distance ("WD") tolerance. The WD is the axial distance between the objective lens 69 and the eye cornea during operation of the camera. Within the boundaries of the WD, unwanted glare and reflected light rays from various surfaces of the eye do not penetrate a physical stop of the imaging optics. A skilled operator of the camera must align the camera at the proper WD from the eye where the illumination footprint on the retina is maximized. The alignment procedure is typically done using an alignment aid. In addition, illumination at this stage of the alignment is performed with non-visible light (such as infrared in the embodiment described) which is not seen by the patient yet is fully within the spectral band of the camera, allowing the operator to optimize the focal position. When the operator decides to capture an image, the infrared spectrum is replaced by the appropriate spectrum in the visible which is required for the specific application.

To fulfill this mode of operation the visible and non-visible illuminating radiation rays must be focused at the same image plane (with overlapping depth of focus). In addition the illumination rays of both spectrums must preferably overlap to comply with the constraint of minimal unwanted glare and unwanted eye reflections.

All optical glasses have a property known as Dispersion (the phenomenon in which the phase velocity of a wave depends on its frequency, or alternatively when the group velocity depends on the frequency). In general, the refractive index is some function of the frequency f of the light, thus n=n(f), or alternately, with respect to the wave's wavelength n=n($\lambda$). As the refractive index varies with wavelength, the angle that the light is refracted by also varies with wavelength, causing an angular separation of the colours known as angular dispersion. This will cause light rays composed of a wide spectrum of visible and non-visible light to be "bent" at a different angle when intersecting an optical lens (similar to colour separation by a prism). This is known as colour aberration.

Due to the effect described above of color aberrations, the objective lens of a camera which is composed of one lens cannot fulfill the broad spectrum imaging and non-glare Illumination constraints described above. However, by introducing a second optical element of different material (and different dispersive properties) such as the shell lens 68 in the inventive solution, the chromatic effects are reduced to some extent and preferably minimized allowing superior operating conditions.

The number of compensating elements is not limited to one correction or shell lens, and in alternative embodiments of the invention other compensating means may be used. The optical surfaces of the compensating element(s) may be either spherical or of any other general surface contour (such as conic aspheric or holographic, for example) or material.

These compensating elements may be designed to correct chromatic aberrations in the illumination channel, the imaging channel, or both. In this embodiment the focus has been on correcting for chromatic aberrations in the illumination channel as the embodiment does not require imaging in NIR and VIS at the same time and has an alternative inventive technique correcting for this, as described in the following paragraph.

When the trigger button 42 is operated to initiate the auto focus routine as previously described (i.e. half pressed) the image preview that is continuously generated by the imaging system 2 is used for the following process. The infrared preview is focused by the optical components onto a slightly different image plane to the visible band. To correct this offset, the imaging system 2 is operable to shift the position of the optical sensor 20 on the optical axis X between the trigger 42 being fully depressed and an image exposure event where the image is captured. The amount of offset is related to characteristics, which may include structure and position of the FOV correction lens 72, the shell lens 68, the objective lens 69, the camera lens 22, and the wavelength of the infrared emitting LEDs 60b, and on focus position. The application software is operable to process and determine the offset required based on the characteristics and generate appropriate control signals to move the optical sensor 20 accordingly at the required time. In alternative embodiments of the invention, the offset is related to other characteristics depending on the imaging being conducted and the components of the module 6.

In another embodiment of the invention, the positioning of the LEDs 60 may be adjusted, or a plurality of sets of LEDs 60 may be provided at different positions as in FIG. 15C), to allow for imaging of various pupil sizes. For small pupil size, the LEDs 60 may be adjusted to be close to the optical axis X, and for normal pupil size, further from the optical axis X. In the case were several sets of LEDs (say two concentric rings of LEDs) are provided, if the pupil is large enough the imaging system 2 is operable to use more LEDs (say the outer set) for flash. In this way shorter exposure times and lower gains can be achieved resulting in improved image quality.

In operation, light emitted from the white LEDs 60a is directed towards the retinal lens system 70. The light is then focussed by the retinal lens system 70 such that the light can penetrate the iris and lens to illuminate the fundus of a patient's eye, for image capture via the optical sensor 20.

Figure 16A:
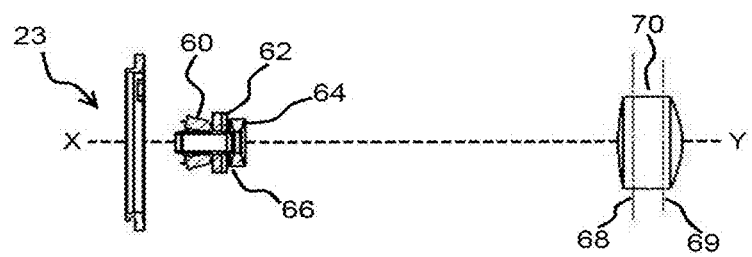
FIG. 16A depicts schematic diagram of optical and other components of the non-mydriatic retina module of FIG. 7.
Figure 16B:
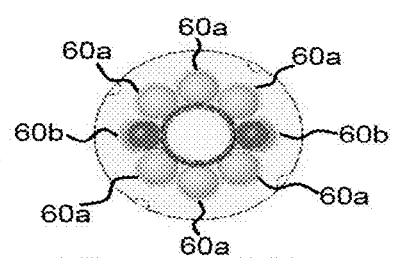
FIG. 16B depicts a front view of placement of LEDs in one configuration of the non-mydriatic retina module of FIG. 7.
Figure 16C:
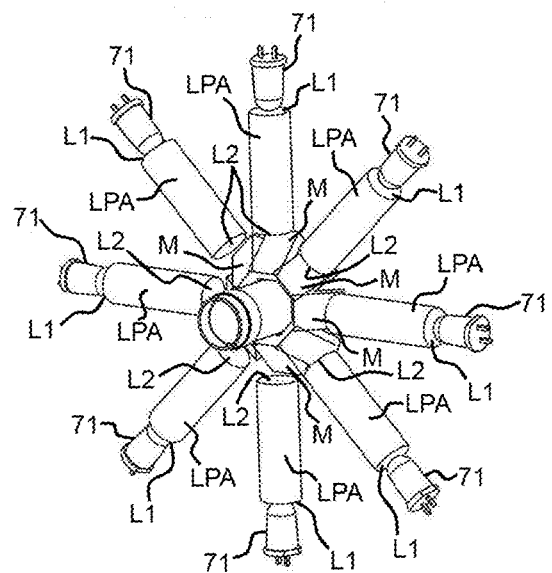
FIG. 16C depicts a schematic diagram of optical and other components of an illumination projection system in another embodiment of the non-mydriatic retina module of FIG. 7.
Figure 16D:
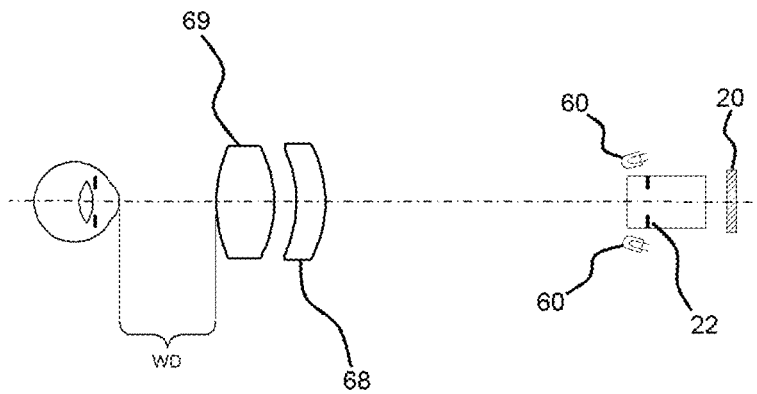
FIG. 16D depicts a schematic diagram illustrating function of the shell lens component of the mydriatic and non-mydriatic retina modules of FIG. 7.

Optical components of the non-mydriatic retinal module 58 are illustrated in FIG. 16A. These are the same as for the mydriatic module 58 as hereinbefore described, except that a wedge or prismatic lens 64 is used to modify the illumination optics.

The prismatic lens is provided in front of the LEDs 60 and acts as a rotationally symmetric prism and may be achieved/approximated using conical surfaces or a negative lens as only the edges are used in the embodiment described. It allows the LEDs 60 to appear closer to the optical axis of the imaging system. This has the benefit of making the image of the ring of LEDs 60 on the cornea smaller and allowing smaller pupil illumination. The prismatic lens 64 is used to shift the apparent position of the LEDs 60 toward the optical axis. To direct the light toward the retinal lens system 70, the LEDs must be angled relative to the optical axis Y.

Figure 8:
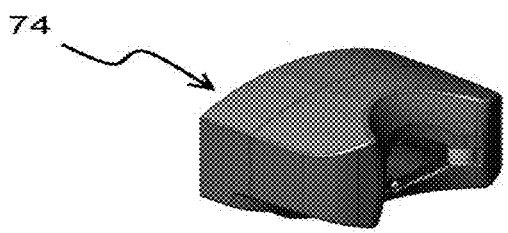
FIG. 8 depicts a front perspective view of a slit module of the imaging system of FIG. 1.

A slit lamp module 74 is illustrated in FIG. 8. The slit lamp module 74 facilitates the following procedures:

capturing images containing a line projected at an angle onto the cornea and iris of an eye to measure the angle between them for the early detection of closed angle glaucoma;

capturing images of a "slit" of light projected at an angle through the lens to see the profile of crystalline lens of the eye;

capturing an image of a "slit" of light incident upon the cornea at an angle magnified enough to view the layers of the corneal surface;

capturing a broadly illuminated anterior segment image; and using the slit lamp as an indirect ophthalmoscope to image a slit projected on the retina.

The optics of the slit lamp module 74 are operable to project a variable thickness "slit" or line of light at a variable angle. The slit is focussed at a focal point of the imager 4 and is coincident with the optical axis X of the imaging system 2 for all angles.

The imaging of the slit lamp module 74 has zoom capabilities equivalent to a x10 to x25 slit lamp. In alternative embodiments of the invention any other zoom factor can be used.

The slit lamp module 74 has variable background illumination to provide a reference for slit lamp images—this is in order to obtain a nicely illuminated background.

Figure 20A:
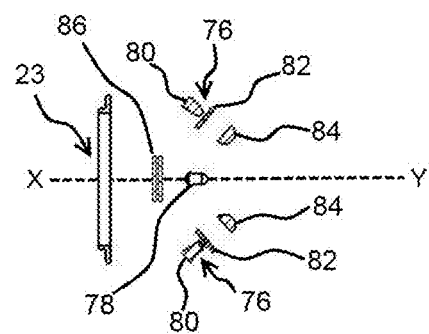
FIG. 20A depicts a top view schematic diagram of optical and other components of a first configuration of the slit lamp module of FIG. 8.
Figure 20B:
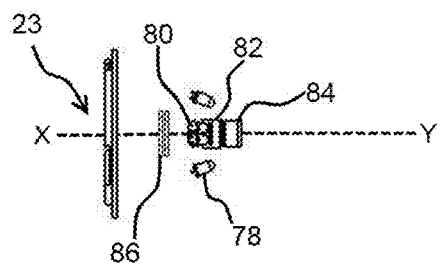
FIG. 20B depicts a side view schematic diagram of optical and other components of the first configuration of the slit lamp module of FIG. 8.

Optical components of a first configuration of the slit lamp module 74 are illustrated in FIGS. 20A and 20B of the drawings. In the embodiment described, the slit is generated from LED sources.

Figure 20C:
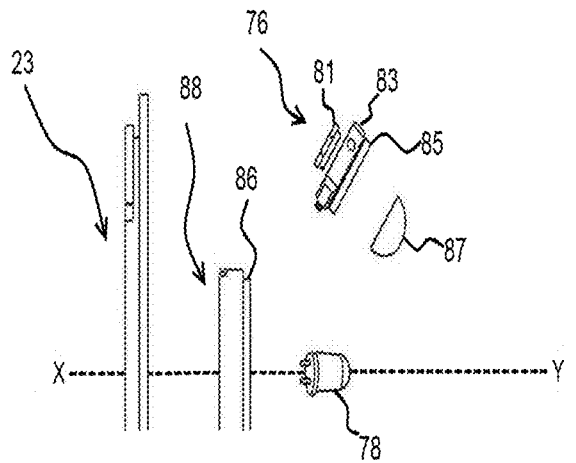
FIG. 20C depicts a top view schematic diagram of optical and other components of a second configuration of the slit lamp module of FIG. 8.
Figure 20D:
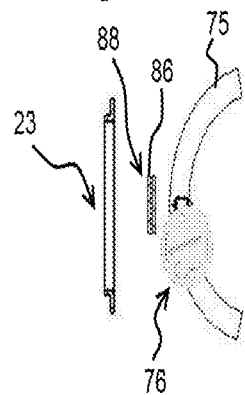
FIGS. 20D and 20E depict top and side view schematic diagrams of optical and other components of a third configuration of the slit lamp module of FIG. 8.
Figure 20E:
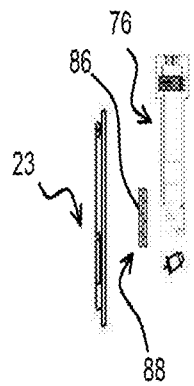

In the first configuration, the slit is generated from an array of low power LED sources (with or without collimation optics) followed by mask and projection optics. In a second and a third configuration, illustrated in FIGS. 20C, and 20D and 20E of the drawings, respectively, the slit is generated from a high power LED source (COD type package), followed by diffusive optics, mask and projection optics.

In the first configuration described, the slit lamp module 74 is designed with fixed parameters, such as slit width, slit angle and slit height, to allow for simplified integration with the application software. In an alternative embodiment of the invention, such as the second configuration, such parameters are variable and appropriate values entered into the application software by the user via the user interface according to a particular set-up. To achieve this in the second configuration described, a slit generation module 76 runs on a curved rail 75 to provide a variable entrance angle. Rotation of a mid section of the slit generation module 76 provides for a variable slit angle (with reduced slit height). The slit height is adjustable with a variable aperture.

Provided in the optical aperture 54 of the slit lamp module 74 are optical components including the slit generation module ("SGM") 76 and radiation emitting means in the form of a background LED 78 operable to emit white light radiation.

It is advantageous for the background LED 78 to be reasonably bright and to have a broad beam to illuminate the whole eye structure. In the embodiment described, this is achieved by having a brightness of approximately 1000 mcd and a projection angle of 50 degrees.

In the first configuration, the SGM 76 comprises radiation emitting means in the form of a slit LED 80 operable to emit white light radiation and aligned with a mask 82. The mask 82 has a rectangular aperture to allow light emitted from the slit LED 80 to shine through in a defined, rectangular, "slit" pattern. Optically aligned with the mask 82 is a cylindrical projection lens 84 to project light passing through the mask 82 onto an eye to be imaged.

In the second configuration, the radiation emitting means of the SGM 76 comprises a high power LED source (COD type package) 81 operable to emit white light radiation and aligned with diffusive optics 83, a mask 85, and projection optics 87. An aperture of the mask 85 has a shape and dimensions (such as slit width, slit angle and slit height) that can be varied, as hereinbefore described, by operation of the user controls to control the light emitted from the LED source 81 shining therethrough. The projection optics 87 are operable to project light passing through the aperture of the mask 85 onto an eye to be imaged. This configuration advantageously provides for brighter illumination in a smaller and simpler design.

In the fixed entry angle slit lamp module configuration described there must be two slit generation modules 76. In a variable entry angle slit lamp module, such as the third described configuration illustrated in FIGS. 20D and 20E, advantageously only one slit generation module is required as it can rotate from one side to the other, to image either of the patient's eyes as required.

Positioned in the aperture 54 along the optical axis Y prior to the SGM 76 and the background LED 78 is an infrared cut filter 86 operable to remove unwanted infrared light present in the LED 78 and as ambient light.

A field of view ("FOV") correction lens 88 is optionally provided in the imaging channel in front of the camera lens 22. This is useful in cases where a slightly different FOV is required from the slit lamp module 74.

Figure 9:
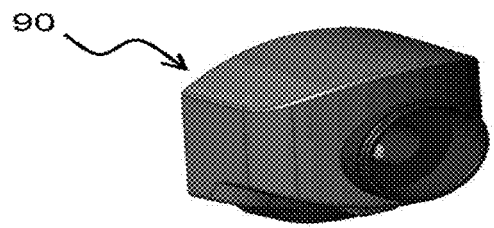
FIG. 9 depicts a front perspective view of a reflex module of the imaging system of FIG. 1.

A reflex module 90 is illustrated in FIG. 9. This module is for imaging the shadow of artefacts in the lens of the eye. The reflex module 90 has two modes of operation: white light preview mode and infrared light preview mode. In infrared preview mode image preview is performed in a dark room with infrared light from an infrared LED 96 that is directed using a dichroic filter or hot minor 100 and beam-splitter 92 into the patients eye and a trigger press initiates an image sequence capture. A first image is the red reflex image (using a white flash from a white LED 94), while the following infrared images document pupil response after the flash and can also give valuable cataract information. In the white light preview mode of operation the preview is performed in white light on a dilated eye and images are captured with a white flash, with the illuminating radiation being emitted from the white LED 94.

Figure 18:
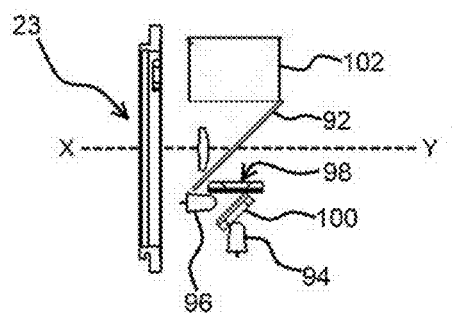
FIG. 18 depicts a schematic diagram of optical and other components of the reflex module of FIG. 9.

Optical components of the reflex module 90 are illustrated in FIG. 18A.

In the reflex module 90, the beam splitter 92 is received within aperture 54. The beam splitter 92 is substantially adjacent the rear face 52. Radiation emitting means in the form of a white light LED 94 operable to emit radiation having a first wavelength—white light radiation, and an infrared LED 96 operable to emit radiation having a second wavelength—infrared radiation are positioned beneath the beam splitter 92 in recesses such that they are set at approximately 90 degrees to each other, with the white light LED 94 arranged to emit light in a direction normal to the optical axis Y, and the infrared LED 96 arranged to emit infrared radiation in a direction parallel to the optical axis Y. The alignment of the white light LED 94 relative to the beam splitter 92 is such that the angle therebetween is approximately 45 degrees.

This configuration of the infrared LED 96 and the white light LED 94 advantageously couples the two beams of different wavelengths. The dichroic filter or hot mirror 100 between the two LEDs reflects all the light from the infrared LED 96 into a coincident beam with the white LED 94 light, such that the illumination of the eye and retina with infrared wavelengths is substantially equivalent to illumination of the eye and retina with visible wavelengths, with resultant improvements in image quality as the image in infra red is the same (minus colour) to the image captured with white light.

The recesses housing the white light LED 94 and infrared LED 96 are separated from the aperture 54 by an illumination aperture 98. Located substantially beneath the illumination aperture 98 and between the white light LED 94 and the infrared LED 96 is a hot minor 100. The hot mirror 100 is angled at 45 degrees to the infrared LED 96 to reflect infrared light emitted therefrom towards the beam splitter 92, through the illumination aperture 98. White light emitted from the white light LED 94 passes through the hot mirror 100. Provided on the opposite side of the beam splitter 92 to the illumination aperture 98 is an absorber 102, operable to absorb light that would otherwise be reflected back into the imaging path or channel.

The illumination aperture 98 operates to restrict illumination angle and prevent significant back reflections from the assembly of the absorber 102.

It is advantageous for the white light LED 94 to be bright in an approximately 20 degree viewing angle. This is advantageous as it provides the reflex module 90 with a 20 degree viewing angle, and adequately fills the illumination aperture with a uniform cross section beam of light such that the eye will be uniformly illuminated and the outer edge of the beam is defined by the illumination aperture rather than the properties of the white LED 94.

It is advantageous for the wavelength of radiation emitted by the infrared LED 96 to provide a high contrast of lens abnormalities, as the applicants have determined that a significant subset of lens abnormalities show an increased contrast in some infra red wavelengths. In the embodiments described, these wavelengths are 790-800 nm but good results can also be achieved with wavelengths between 735 and 900 nm. Increased contrast makes the device more sensitive. Hence for diagnostic purposes one of these wavelengths should be selected in addition to using white light.

The infrared LED 96 preferably also emits radiation in a 20 degree viewing angle for similar reasons as described above in relation to the while light LED 94.

The beam splitter 92 is operable to allow concentric (or coaxial) illumination. 50% is arbitrary but in the embodiment described this provides a good balance between illumination and imaging of the eye.

The depth of field on the eye lens should be small and preferably less then 1 mm. This provides the user with a good sense of depth simply by moving the imaging device in and out (towards and away from the eye). When set up using a chin-rest assembly 103, described in further detail below, the imaging system 2 is operable to take a sequence of images with different foci and reconstruct to a 3D map of features in the eye, such as the eye lens.

In the infrared preview mode of operation, infrared radiation emitted from the infrared LED 96 is reflected by the hot mirror 100, through the illumination aperture 98, and to the beam splitter 92. Upon contact with the beam splitter 92, the infrared radiation is split such that some infrared radiation is reflected along optical axis Y directly towards the patient's eye 103.

In the case of imaging in the white light preview mode of operation, white light emitted by the white light LED 94 passes through the hot mirror 100 and the illumination aperture 98 towards the beam splitter 92. Upon contact with the beam splitter 92, the light is split such that some light is reflected 90 degrees along optical axis Y directly towards the patient's eye 103.

The reflex module 90 is specifically designed to do the tasks that have traditionally been done through modified use of a retinal camera. As can be seen, the reflex module 90 uses dedicated LED sources to project light into the pupil of the eye. It uses projection optics to create the desired beam for entering the pupil, uniform illumination of the retinal in the area of interest to create the reflex and reduction of reflexion artefacts.

The beam splitter 92 couples beams of light from the LEDs into the optical path of the imaging system of the reflex module 90.

Using combined infrared (800 nm wavelength in the embodiment described and in other embodiments between 950 and 735 nm) and white light LED sources results in the production of enhanced non-mydriatic reflex images. Infrared reflex images can be used to augment diagnostic information on cataracts in the eye. Advantages in infrared reflex images include increased contrast in cataracts reflex images.

Once images have been taken using the reflex module 90, the application software is operable to produce an image sequence from the eye that can be used to determine pupil reflex using a combination of the infrared and white light LED sources.

Furthermore, by using a shallow depth of field and image sequence capture with focus control, the reflex module 90 allows a depth montage (simulated deep depth of field) and three dimensional depth profile of scattering sources in the eye to be created.

Figure 10:
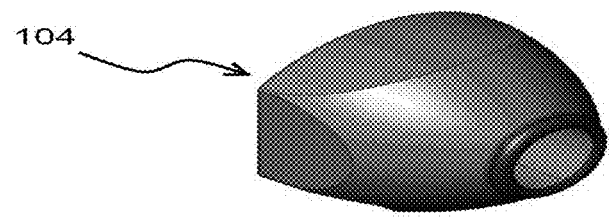
FIG. 10 depicts a front perspective view of a tear film module of the imaging system of FIG. 1.

A tear film module 104 is illustrated in FIG. 10. The tear film module 104 is for analysing the mucous, aqueous and lipid layers on the surface of the cornea of the eye, otherwise known as the tear film and also for examination of the topography of the cornea. The module uniformly illuminates a mask. This mask is then imaged by reflection off the surface of the cornea. The nature of this image is determined by the reflective nature of the tear film and the curvature of the cornea. Abnormalities in either can be detected using the tear film module 104. Analysis from a tear film examination is best performed using the application software on a video of approximately 10 to 30 seconds in length. Without the mask a simple tear film examination can be performed where the film is viewed directly via the imaging system 2.

Figure 19A:
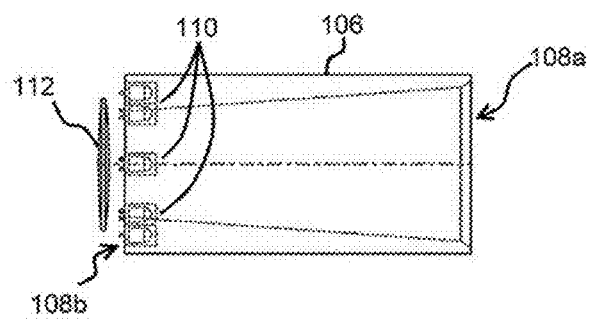
FIG. 19A depicts a schematic diagram of optical and other components of a first configuration of the tear film module of FIG. 10.

Optical components of a first configuration of the tear film module 104, using a side illuminated light guide, are illustrated in FIG. 19A. In this configuration of the tear film module 104, received within the aperture 54 is a hollow cylindrical light guide 106 having open ends 108a and 108b. The light guide 106 is of equal dimension to that of aperture 54, such that end 108a sits flush with the front face 56 and end 108b sits flash with the rear face 52.

Located at open end 108b of the light guide 106 is a plurality of LEDs 110. The LEDs 110 are equidistantly spaced around the circumference of end 108b. The number, and therefore the spacing, of the LEDs 110 is such so as to produce a homogeneous light source, when combined with prismatic array contour on the outer surface and/or scattering points etched into the outer wall of the light guide. A FOV correction lens 112 is optionally provided before the LEDs 110. This is useful in cases where a slightly different FOV is required from the tear film module 104. The light guide 106 is designed to distribute the light from the LEDs 110 evenly, into a distribution that makes the reflexion of the inner surface of the light guide 106 look uniformly lit in the reflected image from the cornea of the eye.

The depth of field on the cornea should at least cover slightly more than the depth of the corneal surface, and the surface of focus of the image of the mask produced by the cornea.

The light guide 106 should be designed to produce a reflexion from the cornea that covers at least the entire cornea.

The light guide 106 is shaped to be a slim conic tube that fits into the orb of the eye 103 or eye socket. The tear film module 104 is adapted to view the tear film in a non invasive manner.

The mask may take the form of an imaged grid provided on the light guide 106 to allow automation of the detection of dry eye in a non invasive manner.

Figure 19B:
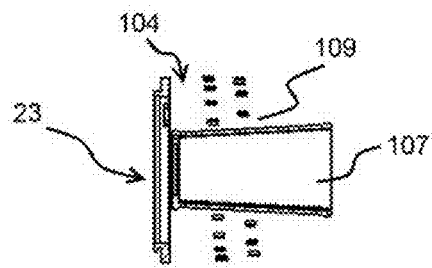
FIG. 19B depicts a schematic diagram of optical and other components of a second configuration of the tear film module of FIG. 10.

FIG. 19B illustrates optical components of a second configuration of the tear film module 104, using a back illuminated light guide.

In this configuration a translucent light guide tube 107 (slightly tapered but having a uniform thickness wall, the outer surface of which is provided with a reflective coating) is illuminated via radiation means in the form of a plurality of LEDs equidistant to each other and the light guide tube 107, around the outer wall surface. Such a cavity design solution overcomes a disadvantage of the side illuminated configuration of thetear film module 104, which can suffer from hot spot resulting from inadequate optical design of the light guide 106.

Preferably, the plurality of LEDs comprises an LED strip received in a spiral groove or cavity 109 proximate the light guide tube 107.

Figure 11:
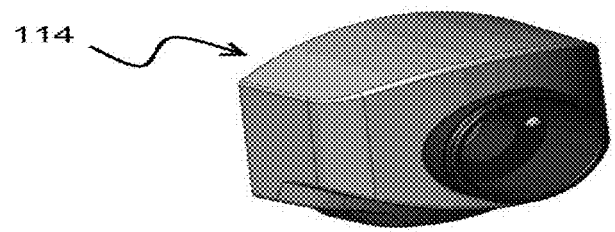
FIG. 11 depicts a front perspective view of a topical fluorescein module of the imaging system of FIG. 1.
Figure 12:
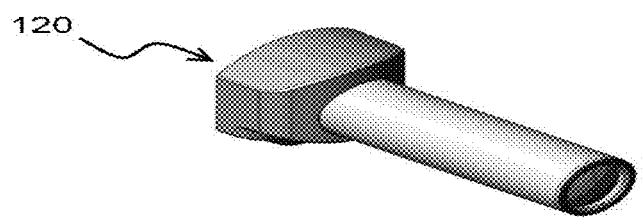
FIG. 12 depicts a front perspective view of a fluorescein angiography module of the imaging system of FIG. 1. Autofluorescence and indocyanine green angiography modules have a similar appearance.

A topical fluorescein ("ToF") module 114 is illustrated in FIG. 11. This module is for imaging the cornea, tear film and tear ducts and meniscus with an applied fluorescein dye.

Figure 17:
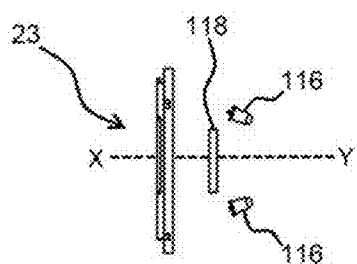
FIG. 17 depicts a schematic diagram of optical and other components of the topical fluorescein module of FIG. 11.

Optical components of the ToF module 114 are illustrated in FIG. 17, and comprise radiation emitting means in the form of two LEDs 116 and a fluorescein filter 118 received within aperture 54 in the path of optical axis Y.

The LEDs 116 are used to evenly illuminate the eye to be imaged. The fluorescein filter 118 is operable to cut out any reflected light directed towards the imager 4. The LEDs 116 have a wavelength of 460 nm, which coincides with the isosbestic point of fluorescein dye. Hence with a standardized application some quantitative measure of depth (independent of tear pH) can be ascertained for image processing via the application software. The specification of the fluorescein filter 118 is such as for use with fluorescein dye, with enough blue transmission for alignment in low fluorescein cases.

Preferably, the depth of field (on the eye) should cover the depth from the tip of the cornea to the tear ducts, being approximately 2-4 mm.

A fluorescein angiography ("FA") module 120 is illustrated in FIG. 11. Autofluorescence and indocyanine green angiography modules have a similar appearance in the embodiment described.

Figure 21A:
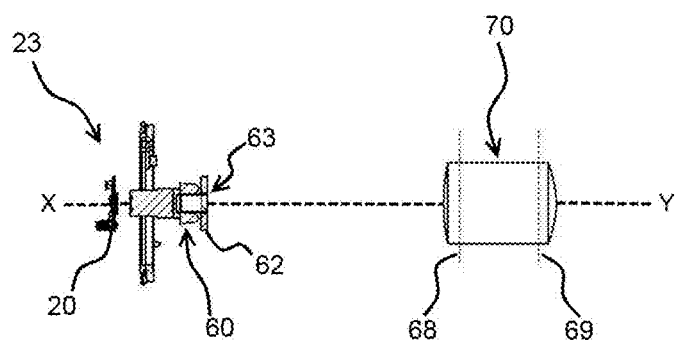
FIG. 21A depicts a schematic diagram of optical and other components of the fluorescein angiography, autofluorescence and indocyanine green angiography modules of FIG. 12.
Figure 21B:
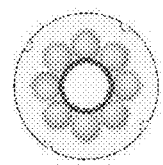
FIG. 21B depicts a front view of placement of LEDs in one configuration of the fluorescein angiography, autofluorescence and indocyanine green angiography modules of FIG. 12.

The FA module 120 is a fundus camera specifically designed for use in a fluorescein angiograph mode of operation. FIG. 21A provides a schematic diagram of optical and other components of the FA module 120, whilst FIG. 21B is a front view of placement of LEDs in one configuration of the FA module 120. In the present embodiment, the FA module 120 is essentially very similar to the mydriatic retinal module 58 as hereinbefore described, and like numerals reference like components thereof, differing in the following respects: the wavelength of illumination is in blue or cyan light (460 nm), imaging is in the red green part of the spectrum (500-650 nm), thereby internal and corneal reflections and scattering in the internal eye lens are not a problem. Consequently, polarisers are not required. Nonetheless, direct reflection should still be avoided as much as possible because the filters are not 100% efficient. Hence the requirement for reflections off the cornea to and scattering from the internal eye lens to be in a direction out of the imaging channel.

The autofluorescence and indocyanine green angiography modules also have a similar structure. In this regard, these modules all use the same principle, whereby illumination is in one wavelength band and imaging is in another wavelength band, and there is substantially no overlap between these two wavelength bands. The modules differ through what bands are used for illumination and imaging. Therefore they use different LEDs and excitation filters 62 and imaging filters 63 (the element inside of 62).

The above and other features and advantages of the embodiment of the invention will now be further described with reference to the system 2 in use.

The user operably connects the imager 4 to the computer 8 via the USB connection, turns them on, and executes the software application.

The user selects an appropriate module 6 from the plurality of modules 6 as hereinbefore described according to the particular ocular examination to be conducted on an eye of a patient, and operably couples the selected module 6 to the imager 4 by engaging their respective bayonet mountings 50 and 18 and interface contacts.

In the embodiment described, the imager 4 (and attached module 6) is lightweight and easily held and positioned by the user as required to conduct the examination via means of the handle 11.

Figure 13A:
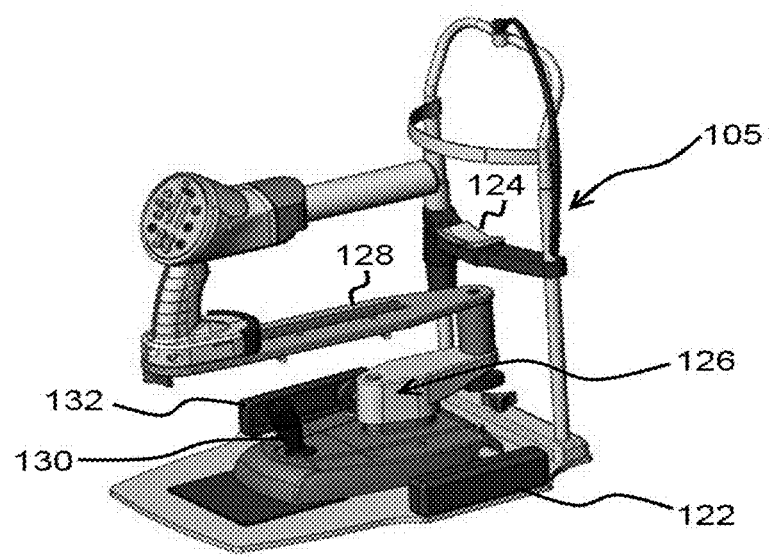
FIG. 13A depicts a rear perspective view of the imager of FIG. 2 having the retina module of FIG. 7 coupled thereto and mounted on a chin-rest assembly at an appropriate working distance.
Figure 13B:
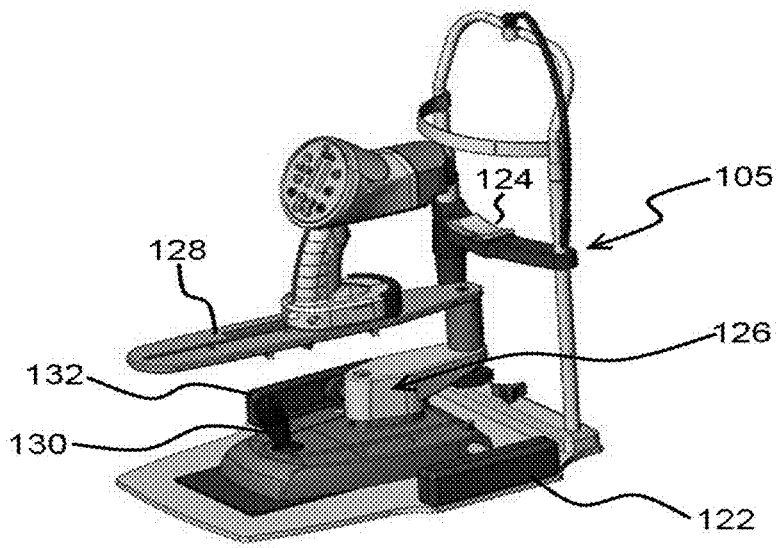
FIG. 13B depicts a rear perspective view of the imager of FIG. 2 having the reflex module of FIG. 9 coupled thereto and mounted on the chin-rest assembly at an appropriate working distance.

Alternatively, the imager 4 (and attached module 6) may be mounted in a chin-rest assembly 105, as illustrated in FIGS. 13A and 13B of the drawings. The chin-rest assembly 105 comprises the following components mounted on a base 122:

an adjustable chin-rest 124, on which the patient may rest their chin during the ocular examination;

a moveable arm 126 having a carriage or cradle 128 for slidably receiving the imager 4 (and attached module 6). The cradle 128 is slidable towards and away from the chin-rest 124 to accommodate working distance requirements of specific modules 6; and a joystick 130 operable to control the moveable arm 126 to align the imager 4 (and the attached module 6) with the patient's eye. Lateral movements of the moveable arm 126 are controlled using standard joystick movement. Elevation of the moveable arm 126 is controlled by rotating the joystick 130A joy stick trigger button 132 is provided on the joy stick 130, providing the same functionality as the trigger button 42.

In this manner the imager 4 can be adapted between hand-held and custom chin-rest use, with all the chin-rest features such as joystick, trigger, autofocus, manual focus, laterality, chin height adjustment, camera height and angle adjustment.

The application software is operable to detect the particular module 6 connected to the imager 4, and display the image being sensed by the optical sensor 20 on the monitor of the computer 8.

The user positions the imager 4 (and attached module 6) and manipulates the user interface/control means of the imaging system 2 until the patients eye is suitably aligned with the optical axis of the imaging path or channel and the desired image is being displayed according to the examination being performed.

As described previously, half press of the trigger button 42 initiates an auto focus process or routine. Alternatively, the user operates the focus wheel 43 to obtain the desired image focus. Once done, the user fully depresses the trigger button 42 which results in the application software operating to execute an image capture sequence, recording the image being sensed by the optical sensor 20 via the imaging path or channel and displayed on the monitor and recording it in a file in the memory of the computer 8.

Relevant processing and post processing are applied to the image or video on the computer 8 and the image data along with any diagnostic information calculated through the processing or post processing are recorded into the database of patient records.

Modifications and variations such as would be apparent to a skilled addressee are deemed to be within the scope of the present invention.

Particularly, it should be appreciated by the person skilled in the art that the invention is not limited to the embodiments described. For example, the invention as described can include the following modifications and/or additions:

Modules having different structures and for different diagnostic purposes, additional to or as alternatives to those described, may be used. Usage of embodiments of devices of the invention for such purposes include: wide angle use for Retinopathy of Prematurity ("ROP"); screening device for Cytomegalovirus ("CMV") retinitis (for HIV/AIDS); and use for imaging/screening of vascular disease such as Alzheimer's disease, cardio vascular disease, stroke or glucose measurement from the eye.

It should be further appreciated by the person skilled in the art that variations and combinations of features described above, not being alternatives or substitutes, can be combined to form yet further embodiments falling within the intended scope of the invention.

Although the present invention and its advantages have been described in detail, it should be understood that various changes, substitutions and alterations can be made herein without departing from the spirit and scope of the invention as defined in the appended claims.

The invention is further described by the following numbered paragraphs:

1. An imager comprising:
   a body; and
   an image sensor supported by the body
   wherein the body is releasably operably coupleable to a module, the module having an optical aperture extending therethrough that aligns with the image sensor when operably coupled to the body to form an imaging channel wherein the sensor is operable to image a subject within an optical axis of the imaging channel.

2. The imager of paragraph 1, further comprising a camera lens for focussing the subject image on the image sensor.

3. The imager of paragraph 2, wherein the camera lens is housed in the body of the imager or in the module.

4. The imager of paragraph 2 or 3, wherein the module comprises projection means for emitting radiation along the imaging channel for radiating the subject for a diagnostic purpose.

5. The imager of paragraph 4, wherein the projection means comprises optics.

6. The imager of paragraph 4 or 5, wherein when the subject is an eye, the camera lens comprises an entrance pupil, wherein the entrance pupil is such that there is substantially no overlap between a conjugate of the entrance pupil and a conjugate of an image of the projection means in a corneal plane.

7. The imager of any one of paragraphs 4 to 6, wherein the projection means comprises radiation emitting means.

8. The imager of paragraph 7, wherein the radiation emitting means comprises one or more light emitting diodes.

9. The imager of paragraph 7 or 8, comprising a selector operable to select a wavelength of the radiation emitted by the radiation emitting means according to the diagnostic purpose.

10. The imager of paragraph 9, wherein when the diagnostic purpose is colour retina imaging, the wavelength selection corresponds to white light; when the diagnostic purpose is fluorescein angiography imaging, the wavelength selection corresponds to cyan light; when the diagnostic purpose is Indocyanine green angiography, the wavelength selection corresponds to infrared light; when the diagnostic purpose is autofluorescence imaging, the wavelength selection corresponds to cyan or amber light; when the diagnostic purpose is retina imaging, the wavelength selection corresponds to white or infrared light; when the diagnostic purpose is slit lamp imaging, the wavelength selection corresponds to white or infrared light; when the diagnostic purpose is tear film imaging, the wavelength selection corresponds to white light; and when the diagnostic purpose is topical fluorescein imaging, the wavelength selection corresponds to cyan light.

11. The imager of any one of the preceding paragraphs, comprising positioning means for moveably positioning the image sensor within the body.

12. The imager of any one of the preceding paragraphs, comprising control means operable to control the sensor and/or the module.

13. A module for an imager having a body and an image sensor supported by the body, the module comprising:
   means for releasably operably coupling to the body; and
   and optical aperture extending therethrough
   wherein, when operably coupled to the body, the optical aperture aligns with the image to form an imaging channel wherein the sensor is operable to image a subject within an optical axis of the imaging channel.

14. The module of paragraph 13, comprising a camera lens for focussing the subject image on the image sensor.

15. The module of paragraph 14, comprising projection means for emitting radiation along the imaging channel for radiating the subject for a diagnostic purpose.

16. The module of paragraph 15, wherein the projection means comprises optics.

17. The module of paragraph 14 or 15, wherein when the subject is an eye, the camera lens comprises an entrance pupil, wherein the entrance pupil is such that there is substantially no overlap between a conjugate of the entrance pupil and a conjugate of an image of the projection means in a corneal plane.

18. The module of any one of paragraphs 15 to 17, wherein the projection means comprises radiation emitting means.

19. The module of paragraph 18, wherein the radiation emitting means comprises one or more light emitting diodes.

20. The module of paragraph 18 or 19, comprising a selector operable to select a wavelength of the radiation emitted by the radiation emitting means according to the diagnostic purpose.

21. The module of paragraph 20, wherein when the diagnostic purpose is colour retina imaging, the wavelength selection corresponds to white light; when the diagnostic purpose is fluorescein angiography imaging, the wavelength selection corresponds to cyan light; when the diagnostic purpose is Indocyanine green angiography, the wavelength selection corresponds to infrared light; when the diagnostic purpose is autofluorescence imaging, the wavelength selection corresponds to cyan or amber light; when the diagnostic purpose is retina imaging, the wavelength selection corresponds to white or infrared light; when the diagnostic purpose is slit lamp imaging, the wavelength selection corresponds to white or infrared light; when the diagnostic purpose is tear film imaging, the wavelength corresponds to white light; and when the diagnostic purpose is topical fluorescein imaging, the wavelength corresponds to cyan light.

22. The module of any one of paragraphs 15 to 21, wherein when the subject is an eye having a retina, the projection means is operable to image the retina.

23. The module of paragraph 22, wherein the projection means comprises a first radiation emitting means emitting radiation in a first wavelength, and a second radiation emitting means emitting radiation in a second wavelength.

24. The module of paragraph 23, wherein the first radiation emitting means comprises a first set of light emitting diodes emitting white light radiation, and the second radiation emitting means comprises a second set of light emitting diodes emitting infrared radiation.

25. The module of paragraph 24, wherein the first set of light emitting diodes and the second set of light emitting diodes are positioned radially with respect to the optical axis of the imaging channel and aligned to generate a beam of radiation that is substantially uniform at an intermediate image plane.

26. The module of paragraph 25, wherein individual light emitting diodes of the second set of light emitting diodes are positioned symmetrically about the optical axis of the imaging channel.

27. The module of any one of paragraphs 15 to 26, comprising reflection removing means for removing reflections from the imaging channel.

28. The module of paragraph 27, wherein the reflection removing means comprises at least one component selected from the group comprising a polariser, an analyser, a stop and/or an aperture.

29. The module of any one of paragraphs 15 to 28, comprising chromatic aberration removing means for removing chromatic aberration from the illumination and imaging channel.

30. The module of paragraph 29, wherein the chromatic aberration removing means comprises a shell shaped lens.

31. The module of any one of paragraphs 15 to 30, comprising optical shifting means operable to shift an apparent position of the projecting means relative to the optical axis of the imaging channel.

32. The module of paragraph 31, wherein the optical shifting means comprises at least one lens selected from the group comprising a prismatic lens, a wedge lens, and a negative lens.

33. The module of any one of paragraphs 15 to 32, wherein the projection means is arranged or operable to facilitate fluorescein angiography, indocyanine green angiography and autofluorescence imaging of the subject.

34. The module of any one of paragraphs 15 to 33, wherein the projection means is arranged or operable to function as a slit lamp.

35. The module of paragraph 34, wherein the projection means comprises background radiation emitting means for illuminating the subject.

36. The module of paragraph 35, wherein the background radiation emitting means comprises a light emitting diode emitting white light radiation.

37. The module of any one of paragraphs 34 to 36, wherein the projection means comprises a slit generation module.

38. The module of paragraph 37, wherein the slit generation module comprises radiation emitting means optically aligned with a mask having a predetermined pattern, wherein the mask is operable to allow emitted radiation to pass therethrough in the predetermined pattern.

39. The module of any one of paragraphs 15 to 38, comprising radiation removing means for removing radiation of a predetermined wavelength from the imaging channel.

40. The module of paragraph 39, wherein the predetermined wavelength is infrared, and the radiation removing means comprises an infrared filter.

41. The module of any one of paragraphs 15 to 40, wherein when the subject is an eye having a pupil, the projection means is arranged or operable to image red and infrared reflex of the eye.

42. The module of paragraph 41, wherein the projection means comprises a beam splitter received within the aperture, a first radiation emitting means emitting radiation in a first wavelength positioned normal to the plane of the aperture, a second radiation emitting means emitting radiation in a second wavelength positioned parallel to the plane of the aperture, and a dichroic filter positioned between the first radiation means and the second radiation means, the dichroic filer and beam-splitter being operable to couple radiation emitted in the first wavelength to radiation emitted in the second wavelength and direct the coupled radiation along the imaging channel into the pupil of the eye.

43. The module of any one of paragraphs 15 to 42, wherein when the subject is an eye having a tear film, the projection means is arranged or operable to image the tear film.

44. The module of paragraph 43, wherein the projection means comprises a light guide containing the optical aperture, and radiation emitting means disposed along a portion of the light guide.

45. The module of paragraph 44, wherein the radiation emitting means comprises a plurality of light emitting diodes equispaced and equidistant radially about the light guide attached to an inner surface of a reflective peripheral wall of the light guide.

46. The module of any one of paragraphs 15 to 45, where the projection means is arranged or operable to facilitate topical fluorescein imaging of the subject.

47. An imaging system comprising:
an imager of any one of paragraphs 1 to 12;
a module of any one of paragraphs 13 to 46 operably coupled to the imager; and
a processor
wherein images captured by the imager are communicated to the processor for storage and/or further processing.

48. An imaging method comprising:
aligning an optical aperture in a module with an image sensor to form an imaging channel; and
imaging a subject within an optical axis of the imaging channel via the image sensor.

49. A computer-readable storage medium on which is stored instructions that, when executed by a computing means, causes the computing means to perform the imaging method of paragraph 48.

50. A computing means programmed to carry out the imaging method as paragraphed in paragraph 48.

51. An imager substantially as hereinbefore described with reference to the accompanying drawings.

52. A module for an imager substantially as hereinbefore described with reference to the accompanying drawings.

53. An imaging system substantially as hereinbefore described with reference to the accompanying drawings.

54. An imaging method substantially as hereinbefore described with reference to the accompanying drawings.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An imager comprising:
a body;
an image sensor supported by the body wherein the body is releasably operably coupleable to a module, the module having an optical aperture extending therethrough that aligns with the image sensor when operably coupled to the body to form an imaging channel and wherein the sensor is operable to image a subject within an optical axis of the imaging channel; and
a camera lens configured to focus a subject image on the image sensor;
a projection means for emitting radiation along the imaging channel for radiating the subject for a diagnostic purpose wherein, when the subject is an eye having a pupil, the projection means is arranged or operable to image red and infrared reflex of the eye, and wherein the projection means includes a beam splitter received within the aperture, a first radiation emitting means emitting radiation in a first wavelength positioned normal to the plane of the aperture, a second radiation emitting means emitting radiation in a second wavelength positioned parallel to the plane of the aperture, and a dichroic filter positioned between the first radiation means and the second radiation means, the dichroic filter and beam-splitter being operable to couple radiation emitted in the first wavelength to radiation emitted in the second wavelength and direct the coupled radiation along the imaging channel into the pupil of the eye.

2. The imager of claim 1, wherein the camera lens is housed in the body of the imager or in the module.

3. The imager of claim 1, wherein the projection means comprises optics.

4. The imager of claim 1, wherein the camera lens comprises an entrance pupil, wherein the entrance pupil is such that there is substantially no overlap between a conjugate of the entrance pupil and a conjugate of an image of the projection means in a corneal plane.

5. The imager of claim 1, wherein the projection means comprises one or more light emitting diodes.

6. The imager of claim 1, comprising a selector operable to select a wavelength of the radiation emitted by the radiation emitting means according to the diagnostic purpose.

7. The imager of claim 6, wherein
when the diagnostic purpose is colour retina imaging, the wavelength selection corresponds to white light;
when the diagnostic purpose is fluorescein angiography imaging, the wavelength selection corresponds to cyan light;
when the diagnostic purpose is Indocyanine green angiography, the wavelength selection corresponds to infrared light;
when the diagnostic purpose is autofluorescence imaging, the wavelength selection corresponds to cyan or amber light;
when the diagnostic purpose is retina imaging, the wavelength selection corresponds to white or infrared light;
when the diagnostic purpose is slit lamp imaging, the wavelength selection corresponds to white or infrared light;
when the diagnostic purpose is tear film imaging, the wavelength selection corresponds to white light; and
when the diagnostic purpose is topical fluorescein imaging, the wavelength selection corresponds to cyan light.

8. The imager of claim 1, comprising positioning means for moveably positioning the image sensor within the body.

9. The imager of claim 1, comprising control means operable to control the sensor and/or the module.

10. A module for an imager having a body and an image sensor supported by the body, the module comprising:
a camera lens for focusing a subject image on the image sensor;
a means for releasably operably coupling to the body;
an optical aperture extending therethrough wherein, when operably coupled to the body, the optical aperture aligns with the subject image to form an imaging channel wherein the sensor is operable to image a subject within an optical axis of the imaging channel; and
a projection means for emitting radiation along the imaging channel for radiating the subject for a diagnostic purpose wherein, when the subject is an eye having a pupil, the projection means is arranged or operable to image red and infrared reflex of the eye, and wherein the projection means includes a beam splitter received within the aperture, a first radiation emitting means emitting radiation in a first wavelength positioned normal to the plane of the aperture, a second radiation emitting means emitting radiation in a second wavelength positioned parallel to the plane of the aperture, and a dichroic filter positioned between the first radiation means and the second radiation means, the dichroic filter and beam-splitter being operable to couple radiation emitted in the first wavelength to radiation emitted in the second wavelength and direct the coupled radiation along the imaging channel into the pupil of the eye.

11. The module of claim 10, wherein the projection means comprises optics.

12. The module of claim 10, wherein when the subject is an eye, the camera lens comprises an entrance pupil, wherein the entrance pupil is such that there is substantially no overlap between a conjugate of the entrance pupil and a conjugate of an image of the projection means in a corneal plane.

13. The module of claim 10, wherein the projection means comprises one or more light emitting diodes.

14. The module of claim 10, comprising a selector operable to select a wavelength of the radiation emitted by the projection means according to the diagnostic purpose.

15. The module of claim 14, wherein
when the diagnostic purpose is colour retina imaging, the wavelength selection corresponds to white light;
when the diagnostic purpose is fluorescein angiography imaging, the wavelength selection corresponds to cyan light;
when the diagnostic purpose is Indocyanine green angiography, the wavelength selection corresponds to infrared light;
when the diagnostic purpose is autofluorescence imaging, the wavelength selection corresponds to cyan or amber light;
when the diagnostic purpose is retina imaging, the wavelength selection corresponds to white or infrared light;
when the diagnostic purpose is slit lamp imaging, the wavelength selection corresponds to white or infrared light;
when the diagnostic purpose is tear film imaging, the wavelength corresponds to white light; and
when the diagnostic purpose is topical fluorescein imaging, the wavelength corresponds to cyan light.

16. The module of claim 10, wherein when the eye includes a retina and the projection means is operable to image the retina.

17. The module of claim 10, wherein the first radiation emitting means comprises a first set of light emitting diodes emitting white light radiation, and the second radiation emitting means comprises a second set of light emitting diodes emitting infrared radiation.

18. The module of claim 17, wherein the first set of light emitting diodes and the second set of light emitting diodes are positioned radially with respect to the optical axis of the imaging channel and aligned to generate a beam of radiation that is substantially uniform at an intermediate image plane.

19. The module of claim 18, wherein individual light emitting diodes of the second set of light emitting diodes are positioned symmetrically about the optical axis of the imaging channel.

20. The module of claim 10, comprising reflection removing means for removing reflections from the imaging channel.

21. The module of claim 20, wherein the reflection removing means comprises at least one component selected from the group comprising a polariser, an analyser, a stop and/or an aperture.

22. The module of claim 10, comprising chromatic aberration removing means for removing chromatic aberration from the illumination and imaging channel.

23. The module of claim 22, wherein the chromatic aberration removing means comprises a shell shaped lens.

24. The module of claim 10, comprising optical shifting means operable to shift an apparent position of the projecting means relative to the optical axis of the imaging channel.

25. The module of claim 24, wherein the optical shifting means comprises at least one lens selected from the group comprising a prismatic lens, a wedge lens, and a negative lens.

26. The module of claim 10, wherein the projection means is arranged or operable to facilitate fluorescein angiography, indocyanine green angiography and autofluorescence imaging of the subject.

27. The module of claim 10, wherein the projection means is arranged or operable to function as a slit lamp.

28. The module of claim 27, wherein the projection means compnses background radiation emitting means for illuminating the subject.

29. The module of claim 28, wherein the background radiation emitting means comprises a light emitting diode emitting white light radiation.

30. The module of claim 27, wherein the projection means comprises a slit generation module.

31. The module of claim 30, wherein the slit generation module comprises radiation emitting means optically aligned with a mask having a predetermined pattern, wherein the mask is operable to allow emitted radiation to pass therethrough in the predetermined pattern.

32. The module of claim 10, comprising radiation removing means for removing radiation of a predetermined wavelength from the imaging channel.

33. The module of claim 32, wherein the predetermined wavelength is infrared, and the radiation removing means comprises an infrared filter.

34. The module of claim 10, wherein the eye has a tear film, the projection means is arranged or operable to image the tear film.

35. The module of claim 34, wherein the projection means comprises a light guide containing the optical aperture, and radiation emitting means disposed along a portion of the light guide.

36. The module of claim 35, wherein the radiation emitting means comprises a plurality of light emitting diodes equispaced and equidistant radially about the light guide attached to an inner surface of a reflective peripheral wall of the light guide.

37. The module of claim 10, where the projection means is arranged or operable to facilitate topical fluorescein imaging of the subject.

38. An imaging method comprising:
in the module of claim 10, aligning the optical aperture with the image sensor to form the imaging channel; and
imaging the subject within the optical axis of the imaging channel via the image sensor.

39. A non-transitory computer-readable storage medium on which is stored instructions that, when executed by a computing means, causes the computing means to perform the imaging method as claimed in claim 38.

40. A computing means programmed to carry out the imaging method as claimed in claim 38.

* * * * *